US011235116B2

(12) United States Patent
Toth et al.

(10) Patent No.: US 11,235,116 B2
(45) Date of Patent: Feb. 1, 2022

(54) LARYNGEAL MASK

(71) Applicant: innoMaskTechnologies Kft., Pereszteg (HU)

(72) Inventors: Zoltan Marton Toth, Sopron (HU); Tamas Olah, Sopron (HU)

(73) Assignee: Innomask Technologies KFT, Sopron (HU)

( * ) Notice: Subject to any disclaimer, the term of this patent is extended or adjusted under 35 U.S.C. 154(b) by 681 days.

(21) Appl. No.: 16/081,495

(22) PCT Filed: Mar. 14, 2017

(86) PCT No.: PCT/HU2017/000020
§ 371 (c)(1),
(2) Date: Aug. 31, 2018

(87) PCT Pub. No.: WO2017/163093
PCT Pub. Date: Sep. 28, 2017

(65) Prior Publication Data
US 2021/0205562 A1 Jul. 8, 2021

(30) Foreign Application Priority Data
Mar. 21, 2016 (HU) .................................. P1600201

(51) Int. Cl.
*A61M 16/04* (2006.01)
(52) U.S. Cl.
CPC . *A61M 16/0434* (2013.01); *A61M 2210/1028* (2013.01); *A61M 2210/1032* (2013.01)
(58) Field of Classification Search
CPC .............. A61M 16/04; A61M 16/0402; A61M 16/0434; A61M 2210/1028;
(Continued)

(56) References Cited

U.S. PATENT DOCUMENTS

| 4,340,046 A * | 7/1982 | Cox ...................... A61M 16/04 128/200.26 |
| 2002/0112728 A1 | 8/2002 | Landuyt |

(Continued)

FOREIGN PATENT DOCUMENTS

| GB | 2445655 A | 7/2008 |
| WO | 2011001437 A2 | 1/2011 |

OTHER PUBLICATIONS

International Searching Authority, Search Report and Written Opinion issued in International Application No. PCT/HU2017/000020, dated Aug. 10, 2017 (12 pgs.).

*Primary Examiner* — Justine R Yu
*Assistant Examiner* — Kelsey E Baller
(74) *Attorney, Agent, or Firm* — Wood Herron & Evans LLP

(57) ABSTRACT

The invention is a laryngeal mask having a head part and an inlet tube, with a passage formed between a laryngeal opening of the head part and an inlet opening of the inlet tube. The laryngeal mask also includes: (1) a covering element encompassing the annular cushion and connected to the outer part of the head part towards the inlet tube from the connection of the annular cushion, where a releasable connection is formed circumferentially in the covering element or at the connection of the head part and the covering element; and (2) a puller element connected to an inner side of the covering element towards the laryngeal opening, and pullable from the inlet tube through the inlet opening, the puller element adapted for removing at least one part of the covering element through the inlet opening of the inlet tube by releasing the releasable connection.

10 Claims, 15 Drawing Sheets

(58) Field of Classification Search
CPC .. A61M 2210/1032; A61M 2025/0018; A61M 25/0067; A61M 39/00; A61M 39/10; A61M 39/14; A61M 39/20; A61M 2039/0009; A61M 2039/085; A61M 2039/1061; A61M 2039/1066
See application file for complete search history.

(56) References Cited

U.S. PATENT DOCUMENTS

| | | | |
|---|---|---|---|
| 2008/0257356 A1* | 10/2008 | Swick ............... | A61M 16/0459 128/207.14 |
| 2009/0194102 A1* | 8/2009 | Chen ................. | A61M 16/0488 128/202.13 |
| 2009/0194114 A1 | 8/2009 | Chen et al. | |
| 2012/0174920 A1* | 7/2012 | Barkai .............. | A61M 16/0409 128/200.26 |

* cited by examiner

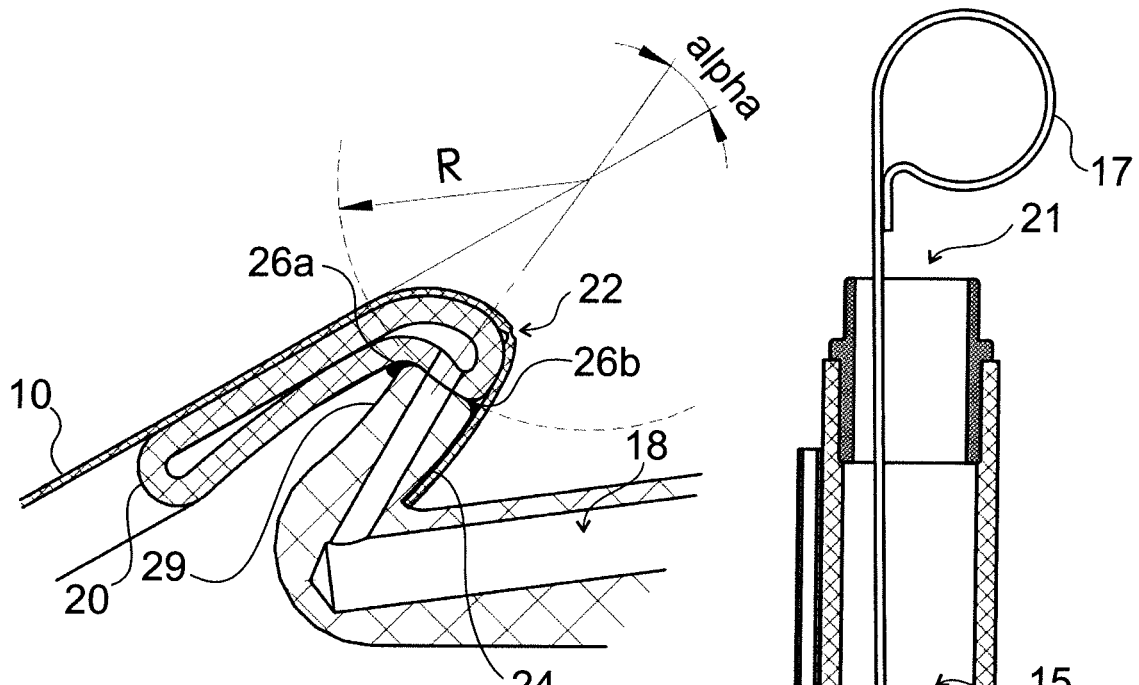
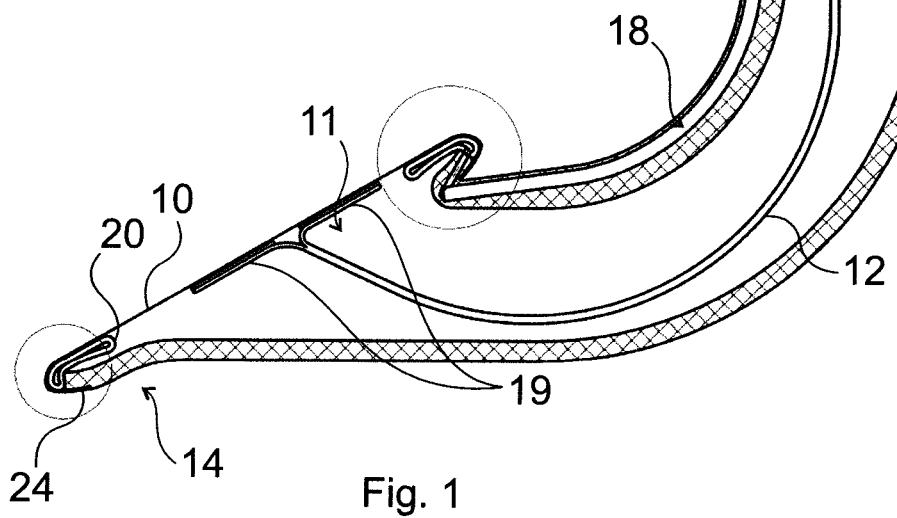

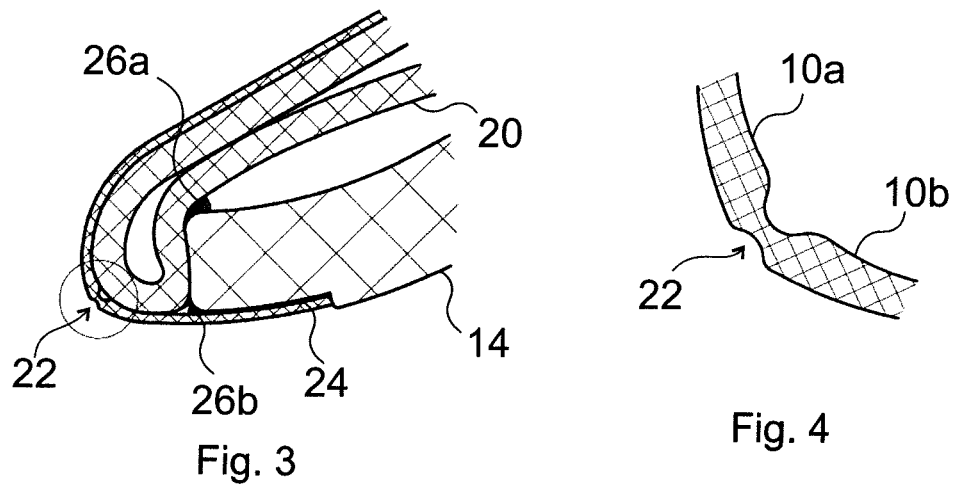
Fig. 3
Fig. 4
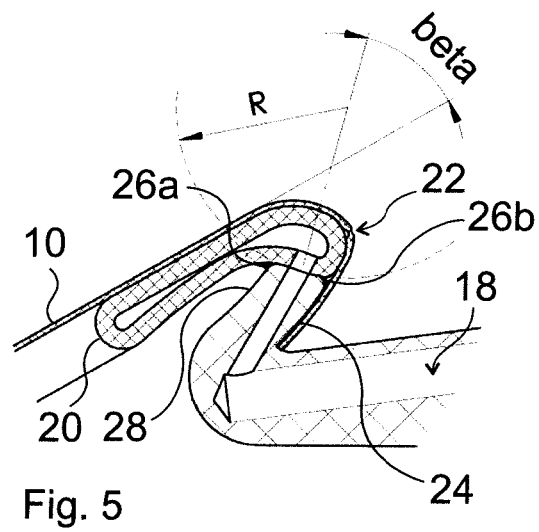
Fig. 5
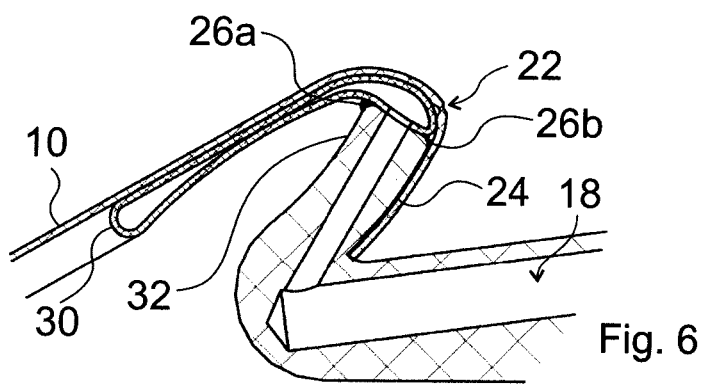
Fig. 6

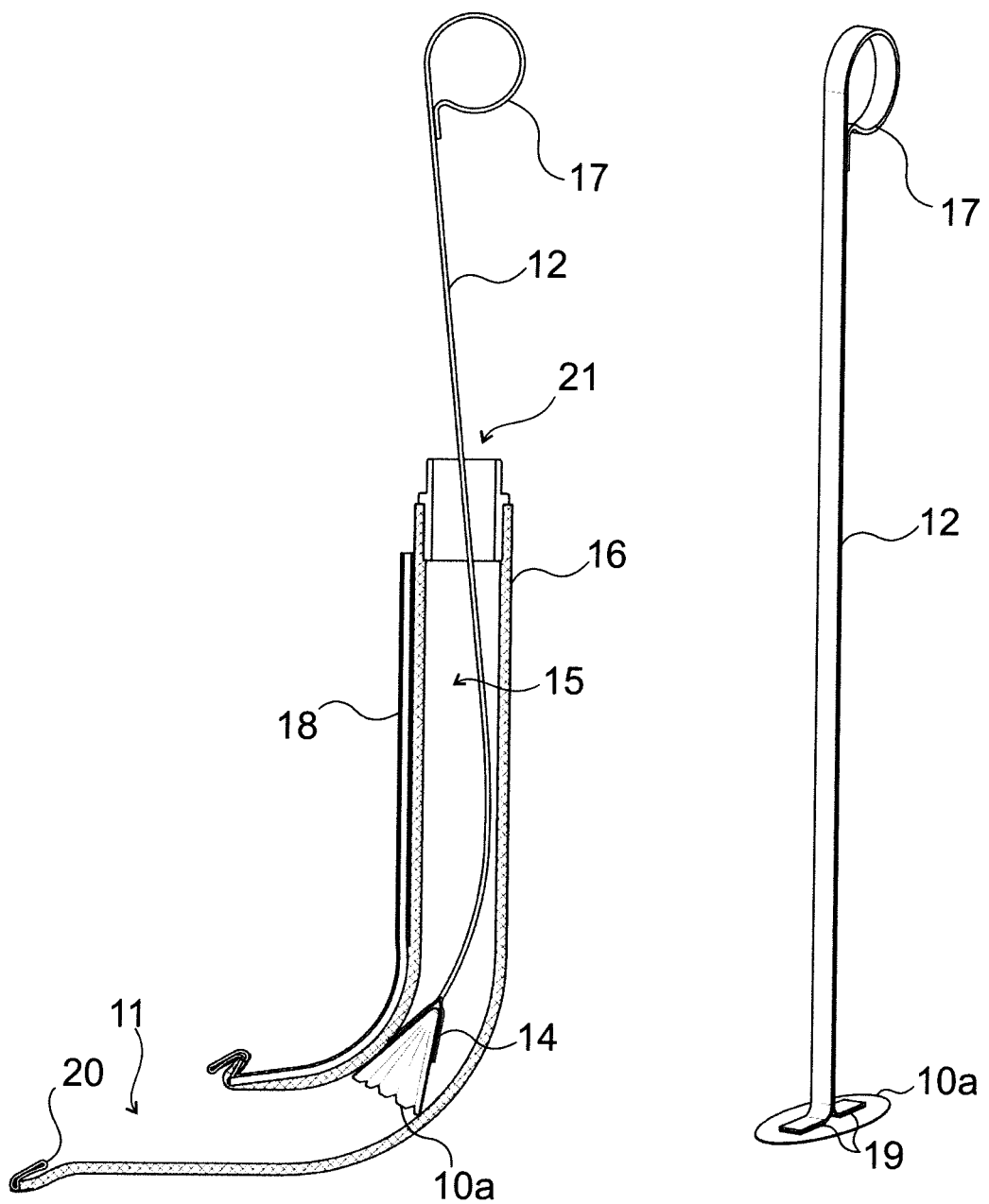

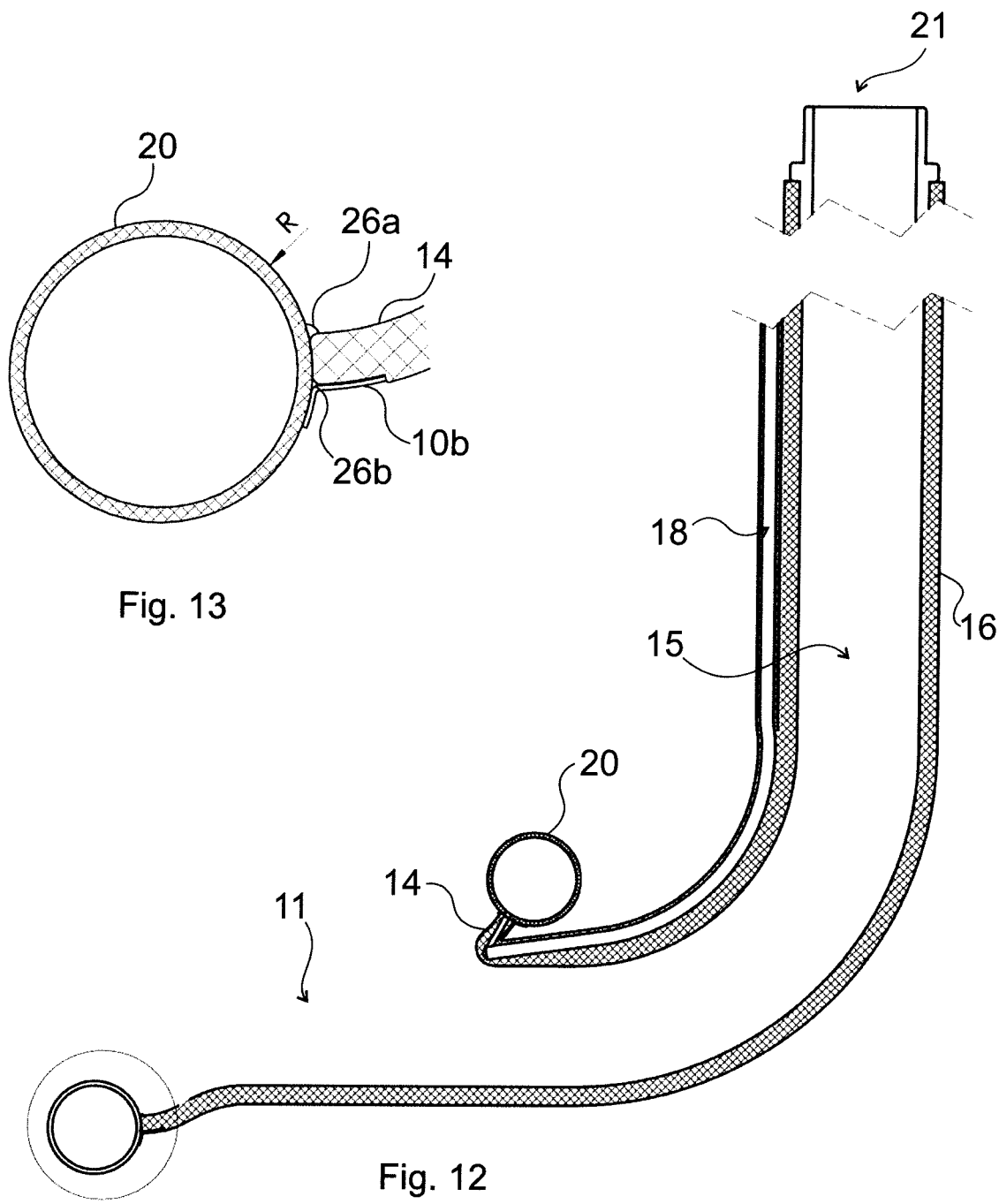

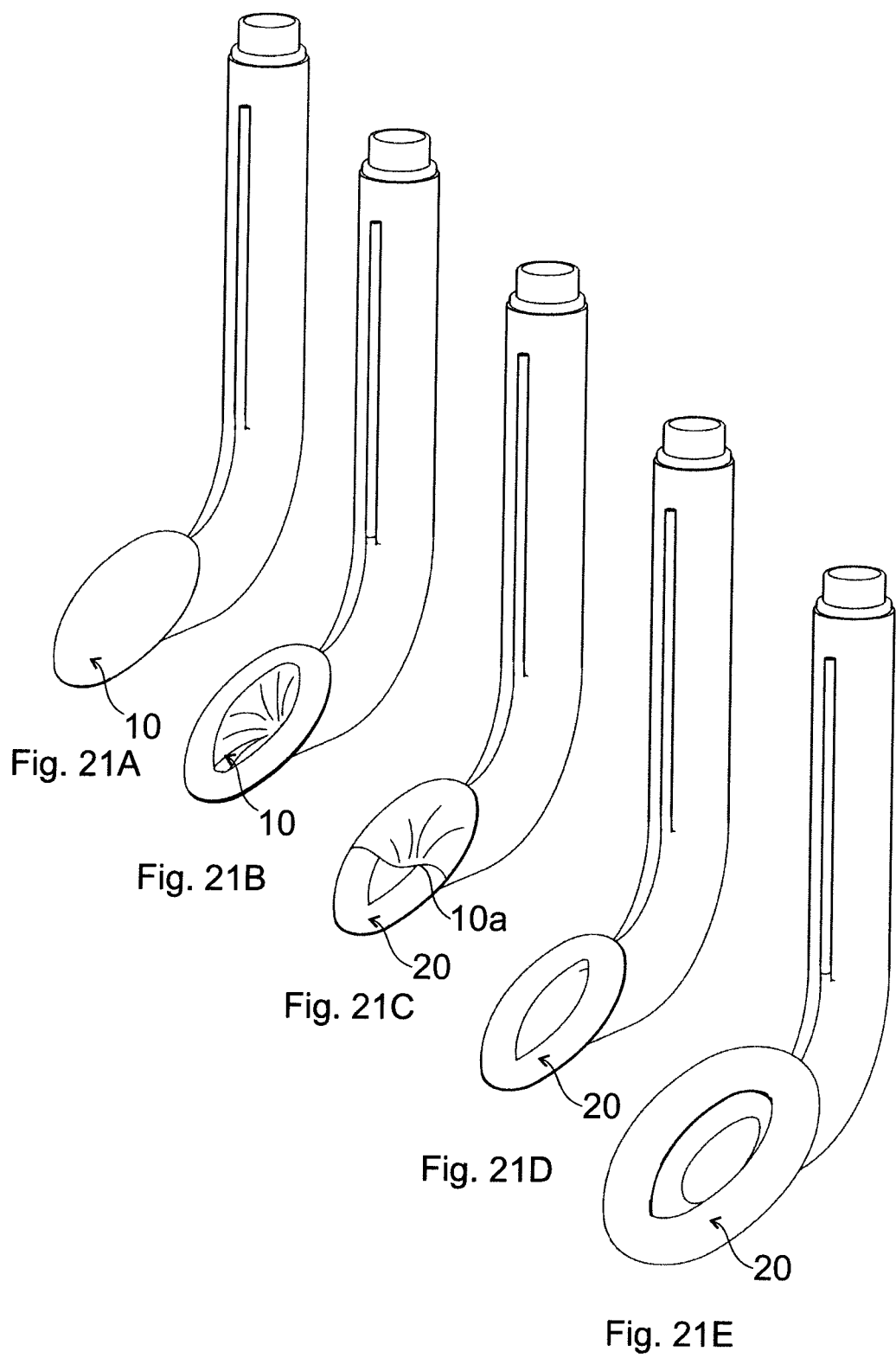

LARYNGEAL MASK

TECHNICAL FIELD

This invention relates to a laryngeal mask comprising a head part and an annular cushion (cuff) adjoined to the said head part.

BACKGROUND ART

The laryngeal mask (or shortly an LMA device—a laryngeal mask airway device) is a medical device applied in anaesthesiology, especially used for narcosis in connection with an operation. The laryngeal mask is to be driven through the oral cavity to its application position, where the opening of the mask lies against the trachea.

For such applications, several laryngeal masks are known.

In US 2003/0037790 A1 a laryngeal mask is disclosed, wherein the annular cushion is connected to the head part on the laryngeal side, i.e. on the head part side facing the trachea. According to FIGS. 7A, 7B, 16A-16C of the document, the insertion of the laryngeal mask until it reaches its application position is carried out in a way that during the process the deflated annular cushion is folded under the head part. The insertion procedure is illustrated by FIG. 17 of the document.

In US 2003/0037790 A1, it is mentioned as a problem of prior art approaches that during insertion, the annular cushion arranged around the head part of the laryngeal mask protrudes so much, and increases the size of the head part so excessively that it behaves as an independent structural component (from the aspect of the insertion procedure of a laryngeal mask, its physical size cannot be disregarded).

In US 2003/0037790 A1, it is suggested as a solution to this problem that the annular cushion should be arranged on the head part on its part facing the trachea, i.e. at its bottom, and not on the side of the head part. However, then as illustrated by FIGS. 15A and 15B of the document, in the case of a patient of given body sizes, the lateral dimensions of the laryngeal mask head part have to be increased to allow the appropriate securing of the annular cushion thereto. This is because in the case of a patient of given body sizes, the dimensions of the annular cushion are determined by the anatomic environment, due to the fact that there is an area at the trachea opening, where the annular cushion must fit in (an annular cushion of appropriate size is associated with given body sizes). Therefore, an inflated annular cushion must have the same lateral size in the case of given body sizes regardless of its attachment to the head part side or to the head part bottom. In a lateral direction, the head part does not protrude beyond the annular cushion, and therefore the anatomic environment also determines the dimensioning of the head part. Therefore, a great disadvantage of the approach described in US 2003/0037790 A1 is that in the case of an annular cushion fixed to the bottom, a head part having larger lateral dimensions (i.e. a wider head part) is to be applied than in the case when the annular cushion is secured laterally (cf. FIGS. 15A and 15B of US 2003/0037790 A1).

According to US 2003/0037790 A1, the annular cushion is folded under the head to make sure that the annular cushion does not behave during insertion as an independent structural component due to its laterally protruding shape, contrary to prior art approaches. Hence, the document suggests the application of such laryngeal masks, where the annular cushion bulges towards the bottom part of the head part. It does not employ the approach based on folding the deflated annular cushion under the head part in the case of a laryngeal mask having a laterally located annular cushion.

However, this solution has several disadvantages. Due to the reasons detailed above, the head part becomes larger in comparison with the lateral annular cushion approaches, and during insertion the annular cushion parts arranged at the bottom of the head part may protrude in an irregular shape, thereby getting caught in surrounding objects and anatomical structures, and therefore in addition to the large head size, this may also make insertion difficult. It is a great disadvantage of the approach that the folded annular cushion may become unfolded (loosened, released, opened) during insertion; because there is nothing which would keep it in place while folded. With an annular cushion of lateral arrangement, a size reduction based merely on folding would presumably work even less, because the folded annular cushion parts would have an even greater tendency to leave their folded positions by their own nature due to the location at which they are connected to the head part. Therefore, the folded state of the annular cushion cannot be maintained on a prolonged basis in a way described in US 2003/0037790 A1 (i.e. by applying simply a folded configuration only), even in the case of a bottom-fixed or laterally fixed annular cushion.

It is a further disadvantage that the annular cushion inserted in its application position is not sterile, because while it is being inserted, it could be soiled by bacteria and foreign materials from the oral cavity (even with the saliva) which is then carried on by the laryngeal mask to the trachea, and what could also happen is that during insertion the loosely folded annular cushion may be punctured by teeth.

The decreasing of head size during insertion is aimed also in patent application WO 2015/015233 A1. However, the document describes an approach to change the head part of a standard laryngeal mask; according to the document, it is recommended to make recesses in the head part to house the deflated annular cushions.

In U.S. Pat. No. 6,761,170 B2, various realizations of a laryngeal mask are described, and each of them is fitted with components which prevent the protrusion of the epiglottis into the laryngeal mask. Hence, the purpose of the approach described in the document is preventing epiglottis from enter into the mask. In the approaches described by the document, the deflated annular cushion laterally protrudes from the laryngeal mask in all implementation examples, and therefore—according to the definition in US 2003/0037790 A1—it behaves as an independent structural component during insertion.

In the implementation examples shown in FIGS. 3 and 4 of U.S. Pat. No. 6,761,170 B2, the entering of epiglottis into the laryngeal mask is intended to be prevented by a tape, which is secured longitudinally to the annular cushion. The tape is attached only to the annular cushion, and it is not connected to the head part. This tape is fixed to the deflated annular cushion in a way to press it down and to flatten it, and therefore the deflated annular cushion protrudes laterally along the periphery of the laryngeal mask, as shown in FIGS. 3 and 4 of U.S. Pat. No. 6,761,170 B2. The pressing down and flattening increases the lateral protrusion of the annular cushion compared to the loose or inflated state thereof. Therefore, the tape serves for preventing the protrusion of the epiglottis, and it can be removed once the mask is driven to its application position. It is a great disadvantage of this this implementation example of the approach described by the document that the tape is removed outside the laryngeal mask, and therefore when the tape is removed, this may cause injuries along the route of insertion. Furthermore, according to the document, the tape is arranged loosely, and therefore it may even be easier for it to be caught in protruding objects (e.g. a tooth).

In the implementation example of FIG. 5 of U.S. Pat. No. 6,761,170 B2, the protrusion of the epiglottis into the laryngeal mask is prevented by an insert fitted into the mask. The end part of the insert is aligned with the laryngeal mask side facing the trachea when the laryngeal mask is inserted. According to this implementation example of U.S. Pat. No. 6,761,170 B2, the insert preventing the protrusion of the epiglottis does not press down the annular cushions, i.e. in this implementation example the movement of the annular cushions is even less restricted than in the other implementation example described above.

A further implementation example is shown in FIG. 2 of the document, where the protrusion of the epiglottis into the laryngeal mask is prevented by an inflatable bag-like member. Each embodiment depicted by way of example uses a different method for avoiding the protrusion of the epiglottis into the laryngeal mask, and the document does not provide a teaching regarding the combination of the various implementation examples.

Approaches to prevent the entering of epiglottis into the laryngeal mask during insertion are disclosed also in U.S. Pat. No. 6,698,430 B2 and US 2009/0194114 A1.

A common disadvantage of laryngeal masks having a laterally arranged annular cushion is that while being driven to their application position, the deflated annular cushion behaves as an independent structural component, making the insertion difficult. According to the discussion above, it is a general disadvantage of known laryngeal masks that during insertion, their annular cushions may be caught in surrounding objects (e.g. teeth), since—even when folding is applied—the cushion is positioned at random and therefore it may have protruding parts.

In view of known approaches, there is a demand for a laryngeal mask, wherein the disadvantages mentioned above are avoided as much as possible, for example wherein the effective head size prevailing during the insertion of the mask can be efficiently reduced in comparison with known approaches, and wherein preferably certain other disadvantages characterising the known approaches do not arise.

DESCRIPTION OF THE INVENTION

The primary object of the invention is to provide a laryngeal mask, which is free of disadvantages of prior art approaches to the greatest possible extent.

A further object of the invention is to provide a laryngeal mask, with which the effective head size prevailing during the insertion of the mask can be efficiently reduced in comparison with known approaches.

Furthermore, an object of the invention is to provide a laryngeal mask, wherein the annular cushion is arranged while driving the mask to its application position in a way to prevent bulging (according to the terminology applied in the introduction, in a way that it is not an independent structural component) and furthermore the annular cushion getting caught in the objects of the involved anatomic environment can be avoided.

The objects of the invention can be achieved by the laryngeal mask according to claim 1. Preferred embodiments of the invention are defined in the dependent claims.

BRIEF DESCRIPTION OF THE DRAWINGS

Preferred embodiments of the invention are described below by way of example with reference to the following drawings, where FIG. 1 is a side section view of an embodiment of the laryngeal mask according to the invention, FIG. 2 is a magnified drawing of a part encircled in FIG. 1, FIG. 3 is a magnified drawing of a second part encircled in FIG. 1, FIG. 4 is a magnified drawing of the part encircled in FIG. 3, FIG. 5 is a drawing of a further embodiment of the invention with a detail similar to that in FIG. 2, FIG. 6 shows a yet further embodiment of the invention with a detail similar to that in FIG. 5, FIG. 10 illustrates the embodiment of the invention of FIG. 1, in a further phase of removing the appropriate part of the covering element, FIG. 11 is a perspective view illustrating the puller element connected to the covering element of a laryngeal mask according to the invention, FIG. 12 shows the status in the embodiment of FIG. 1, when after the removal of the appropriate part of the covering element, the annular cushion is already inflated, FIG. 13 shows a magnified drawing of the part encircled in FIG. 12, FIGS. 21A to 21E are side perspective views of the phases of FIGS. 20A to 20E, FIGS. 22A to 22E are sectional views of the various realization options of a releasable connection.

MODES FOR CARRYING OUT THE INVENTION

Figure 7:
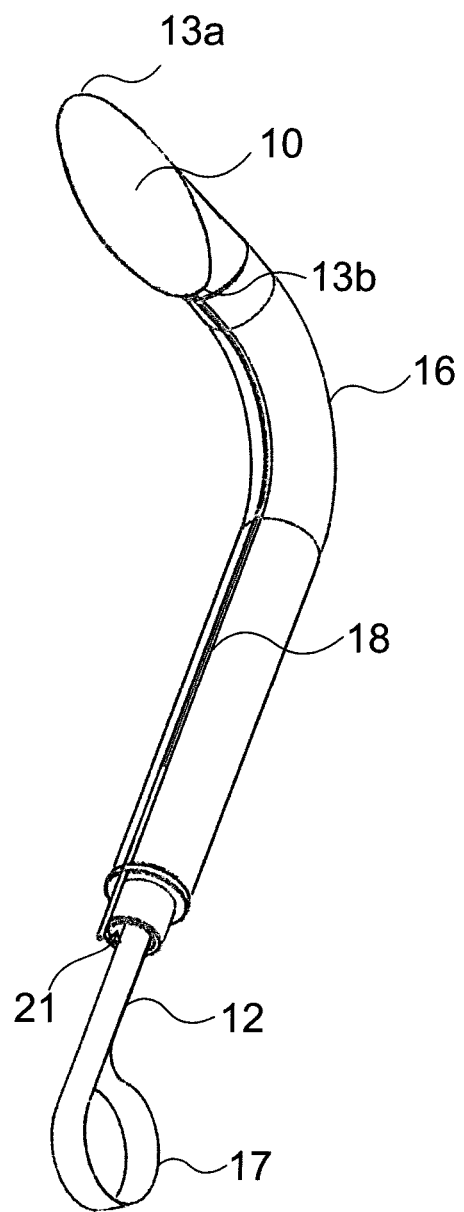
FIG. 7 is a perspective view illustrating the embodiment of FIG. 1 of the laryngeal mask according to the invention.

In FIG. 1 an embodiment of the laryngeal mask according to the invention is shown in a sectional side view. The laryngeal mask according to the invention comprises in the present embodiment a head part 14 and an inlet tube 16 connected (attached) to the head part 14, and a passage 15 is formed between a laryngeal opening 11 of the head part 14 and an inlet opening 21 of the inlet tube 16, the laryngeal opening 11 is adapted for fitting onto a trachea, and the inlet opening 21 of the inlet tube 16 is opposite the connection of the inlet tube 16 with the head part 14. The passage 15 is shown in FIG. 1; in the embodiment illustrated by the figure, the laryngeal mask has a contiguous inner space between the laryngeal opening 11 and the inlet opening 21. A type of passage similar to the passage 15 is formed in all known laryngeal masks, originating from the purpose of the device.

The laryngeal mask according to the invention is a laryngeal device, with its main structural parts being the head part (with the annular cushion) and the inlet tube connected to it.

In the embodiment according to FIG. 1, the head part 14 and the inlet tube 16 are made from one piece. Accordingly, the boundary between the head part 14 and the inlet tube 16 is not shown in FIG. 1; the head part is practically that part of the laryngeal mask—widening in the present embodiment—which can be placed on the trachea, and to which the inlet tube leads. Such embodiments are conceivable (in accordance with similar prior art approaches), where the head part and the inlet tube are made from separate pieces.

In the present embodiment, the laryngeal mask according to the invention further comprises an annular cushion 20 connected to an outer (external) part of the head part 14 around the laryngeal opening 11. According to the figures, the annular cushion 20 is connected circumferentially (all around) to the head part 14 in the present embodiment. FIG. 1 is a sectional view illustrating the connection of the deflated annular cushion 20 and the head part 14. FIG. 12 is a sectional view illustrating the connection of the inflated annular cushion 20 and the head part 14. FIGS. 18, 19, 20E and 21E are perspective views showing the connection of the annular cushion 20 and the head part 14.

In the embodiment of the invention according to FIG. 1, the laryngeal mask further comprises a covering element 10 encompassing the annular cushion 20, folding it back to the head part 14 and covering the laryngeal opening 11, the covering element 10 is connected to the outer part of the head part 14 at a part being towards the inlet tube 16 from the connection of the annular cushion 20. As shown also in the figures, the description that the covering element 10 encompasses (surrounds) the annular cushion means that the covering element 10 totally surrounds and covers the folded back annular cushion 20, and furthermore that the covering element 10 fully covers the laryngeal opening also, i.e. the covering element 10 is pulled as a bag over the annular cushion 20 and the head part 14. Furthermore, the covering element 10 is preferably arranged tightly.

In the embodiment of the laryngeal mask according to FIG. 1, the covering element 10 is connected to the outer part of the head part 14 by being arranged around it from the connection of the annular cushion 20 to the part which is towards the inlet tube 16. To make sure that the protrusion of the annular cushion surrounded by the covering element is avoided in the initial state of the laryngeal mask (i.e. when the releasable connection to be introduced below has not been released yet) the connection of the covering element to the head part may also be formed in a way that the connection does not run all around, but by way of example it is interrupted at certain points. If the sections interrupting the connection are short (for example, dotted adhesive is applied circumferentially or the connection is provided with interrupted ultrasonic welding with interruption spaces of 1 to 2 mm), it can still be ensured that the annular cushion does not bulge from under the covering element, in the unreleased state of the releasable connection. In this case the annular cushion cannot carry any contamination with it, because it is covered by means of the covering element.

According to the invention, a releasable connection (detachable connection) is formed circumferentially (running all around, roundgoing) in the covering element—in the covering element 10 in the embodiment of FIG. 1—or at the connection of the head part and the covering element. As described below, the releasable connection can be formed by way of example by a thinning, a split perforation (perforation with splits, incisions) or a hole line perforation (the releasable connection can also be formed in other ways). The thinning runs all (completely) around along a periphery (circumference) of the covering element (preferably around the head part, see for example FIG. 1). In the case of a releasable connection formed by perforation, "formed circumferentially" means that the interruptions (splits, holes) are arranged with such a density along the full length of the releasable connection that they provide for the planned and controllable nature of releasing the releasable connection (i.e. the interruption) circumferentially. Subject to the pulling (tensile) force applied, the accurate configuration of perforation (the ratio of splits and holes compared to the connection parts between them) can be determined. As a result therefore, when the puller element is pulled with an appropriate force, the releasable connection is released (torn) in its full length, and the removable part of the covering element become separated. By using such a configuration of the releasable connection, it can be provided that its releasing (tearing) can be planned and controlled along the whole periphery, i.e. to make sure that the releasing is not incidental.

The annular cushion cannot carry any contamination with it in the case when the releasable connection is formed, for example, with a split perforation or hole line perforation, because it is covered (separated) by means of the covering element (the eventually contaminated covering element is removed, but the annular cushion stays in its application position for a prolonged period, and therefore its clean and uncontaminated condition plays a greater role). In the embodiment of FIG. 1, the connection between the covering element 10 and the head part 14 runs preferably all around the head part 14, and the releasable connection is formed by means of the thinning 22, and therefore, due to the total 'separation' of the annular cushion 20, the complete sterility of the annular cushion is provided up to the moment when the covering element is removed (for details, see below).

The material of the covering element is selected in a way that it meets the so-called medical grade requirements; accordingly, the material of the covering element may be a kind of silicone or PVC (polyvinyl-chloride). Preferably, PVC (or its derivatives) is used as the material of the covering element, because its tearing characteristics can be planned better than those of silicone. Basically, the elongation characteristics of silicone can be designed; in addition, a covering element with tearing characteristics which can be designed to a sufficient extent can also be made from silicone. Hence, the covering element (cover layer) is a flat and thin sheet, the material of which is preferably silicone or PVC. The material of the annular cushion may also be silicone or PVC.

In the present embodiment, the laryngeal mask further comprises a puller element 12 being connected to an inner side of the covering element 10 being towards (facing) the laryngeal opening 11, being arranged in the passage 15 and being pullable from the inlet tube 16 through the inlet opening, and being adapted for removing at least one part of the covering element 10 through the inlet opening 21 of the inlet tube 16 by releasing the releasable connection. In the present embodiment, the covering element 10 may only be removed partly by means of the puller element 12 (only one part of it, which is located at that side of the thinning 22 to be described below being towards to the connection of the puller element 12, i.e. covering element part 10a can be removed). The thinning 22 is a releasing line, along which the covering element 10 has a smaller thickness compared to the surrounding areas. Since the puller element 12 is arranged as described above, the removable part of the covering element 10 leaves the laryngeal mask through the inlet opening 21 of the inlet tube 16 when this part is removed, i.e. it can be removed by guiding it inside the device, and therefore the removal of the covering element or of an appropriate part thereof may not cause an inner traumatic injury.

In such an embodiment, however, where the releasable connection runs all around at the connection of the head part and the covering element (for example, by the pre-planned weakenings of the adhering), the whole covering element is removed, because in such embodiments when the releasable connection is released by the puller element, the covering element can be separated from the head part. Therefore, in certain embodiments of the invention, the complete covering element can be removed by releasing the releasable connection.

The arrangement position of the releasable connection determines how large part of the covering element can be removed by the puller element (the releasable connection is arranged in the covering element or at the connection of the head part and the covering element), because as a result of pulling the puller element outwards, only the releasable connection is released, the covering element does not tear (break, split) elsewhere (and of course neither does the puller element) and hence the covering element part connected to the puller element and located within (surrounded by) the releasable connection is removed. Therefore, the releasable connection defines a planned releasing (separation) site (in most cases a line). As described below, the releasable connection can be formed in various ways (by the thinning the covering element, using a split perforation or a hole line perforation or even an adhesive of appropriate strength) in a plannable (planned) manner, i.e. ensuring that through the application of a certain pulling force the releasable connection is released. Of course, to this end, a puller element and a covering element of appropriate strength is to be applied.

It is shown in FIG. 7 that in this embodiment, the head part 14 has a shape narrowing towards (tapering towards) its front end 13a and its rear end 13b, and—as shown in FIG. 1—the puller element 12 is connected to the covering element 10 by two connecting feet 19, each of them extending towards the front end 13a and the rear end 13b, respectively.

Therefore, FIG. 7 shows the front end 13a and the rear end 13b of the head part 14. (In FIG. 7, the ends of the head part 14 are covered by the covering element 10, and therefore the reference symbols indicate the positions of the ends). FIG. 7 also shows the narrowing shape of the head part towards the ends; this narrowing shape is substantially oval, and in the case of certain prior art laryngeal masks it has a shape of an almond. The connecting feet 19 are adhered to the covering element 10 according to the figure. Ultrasonic welding (ultrasonic welding using an auxiliary material or ultrasonic welding without an auxiliary material) or a different suitable way of fixing can be applied instead of adhering. As shown also in FIG. 11, in the present embodiment, the puller element 12 is only connected via the two connecting feet 19 to the covering element 10; this is necessary for accomplishing the effect described below.

Thanks to the connection applying the connecting feet 19 between the covering element 10 and the puller element 12 according to the present embodiment, the releasing of the releasable connection (for example, tearing of the thinning 22) will preferably start at one of the ends of the head part 14 (depending also on how long each connecting foot is, i.e. where exactly is the place where the two connecting feet meet), preferably at its front end 13a. Hence, by the help of the connecting feet, the place where the releasing (breakage) starts can be planned, and by the help of the connecting feet located as described above, the place where the releasing starts can preferably be positioned to the front end 13a or to the rear end 13b.

In the case of other type of joining of covering element-puller element, by applying an appropriate pulling force, the releasing (tearing, breakage) starts somewhere along the releasable connection, in most cases at the place where the pulling force is mostly concentrated. With the help of the application of various numbers and locations of connecting feet, the place, that is the starting position of the tear as well as the required pulling force can be pre-planned, i.e. the tearing can be controlled with the various types of connecting feet. By means of the connecting feet design described above (which has the connecting feet 19), the pulling force can be concentrated on the ends of the head part 14.

The configuration of the connecting foot 19 is shown in the perspective view of FIG. 11. At the end of the puller element 12 protruding from the inlet tube 16, a loop 17 is formed; by means of this loop 17 the puller element 12 can be grasped well when it is pulled out of the inlet tube 16. It is not necessary in any case to form the loop, the end part of the puller element could be grasped without any auxiliary elements, and it is also conceivable that there is a different element at the end of the puller element for facilitating the grasping.

It is furthermore shown in FIG. 1 that an air inlet passage 18 runs along the inlet tube 16, with the inlet part thereof leading to the annular cushion 20 being shown in FIG. 2. The air inlet passage 18 may be formed in a number of known ways, and in fact it may also be integrated into the wall of the inlet tube along its whole length. As shown by the other figures, the passage 18 runs along the inlet tube 16 arranged on its outside, then leads to the wall of the head part 14, and when it exits through an edge 29, it goes into the annular cushion 20, on which an aperture matched to the end of the passage 18 is formed as shown in FIG. 2.

FIG. 1 also illustrates that the covering element 10 folds back the annular cushion 20 to the head part 14, i.e. the annular cushion 20 is arranged next to the head part 14, in its circumferentially folded back position by the covering element 10. The covering element 10 preferably has a tight arrangement, and therefore maintaining the folded back position of the annular cushion 20 is ensured. It is shown also in FIG. 1 and can be even better observed in further figures that the covering element 10 is arranged in a way to fold back relatively tightly the annular cushion 20, but this folding back is not done to such an extent that for example it is broken, or subjected to permanent deformation. A deformation of undesirable extent can be avoided by the appropriate dimensioning of the covering element 10 (i.e. how loose or tight it is); and on the basis of knowing the dimensions of the annular cushion 20 and the head part 14, such a covering element can be designed which, for example, according to FIG. 1, using an adhesive layer 24 to connect preferably circumferentially to the head part 14 (in other embodiments it may even be connected by ultrasonic welding) and it folds back the annular cushion 20 to the head part 14 according to the criteria above, i.e. by avoiding the crushing of the annular cushion, while keeping tight the laryngeal opening 11 covering part of the covering element 10.

The annular cushion is preferably folded back to the bottom of the head part, i.e. in a way that it partly covers the laryngeal opening, but a further embodiment is also conceivable where according to the description below, by means of the covering element, the annular cushion is folded back to the upper part of the head part in a way that the covering element encompasses the annular cushion.

Regarding this case, again reference is made to FIGS. 1 and 2. It is conceivable on the basis of the figures that the annular cushion is folded back to the outer side of the head part. In this case the covering element cannot be connected to the head part in a way shown in the figure, because on the already used connection part the folded back annular cushion is arranged, but the covering element may be connected to a part of the head part which is even closer to the inlet tube, similarly to the embodiment of FIG. 1 even so that it lies on it on a surface, and the adhesive layer is arranged on this surface either in a way that the covering element is adjoined to the head part along a line, or in other similar ways.

In the embodiment of FIG. 1, the head part 14 is formed so that it has a relatively narrow circumferential edge 29, the end part of which faces circumferentialy outside. The annular cushion 20 is fixed circumferentially by adherings 26a and 26b to the end part facing circumferentially outwards.

It is noted that in embodiments which are identical with the present embodiment in all other aspects, for example, ultrasonic welding (ultrasonic welding using an auxiliary material or ultrasonic welding without an auxiliary material) or a different suitable fixing method may be applied instead of the adherings 24, 26a, 26b for attaching/fixing the appropriate elements to each other.

The adherings 26a and 26b are also shown in FIGS. 2, 3, 5 and 6. The position (arrangement) of the annular cushion 20 in its inflated state is determined by the connection applying the adherings 26a, 26b (this works also when the connection is made by ultrasonic welding or a different suitable securing method, if it is applied circumferentially along two lines similarly to the adherings 26a, 26b), because the annular cushion 20 will be principally stretched by means of the said adherings 26a, 26b on the edge 29, and it will be arranged accordingly around the head part 14.

The edge 29 of head part 14 shown in FIG. 2 has such an end part, i.e. a part suitable for adjoining the annular cushion, which does not face the plane determined by the laryngeal opening in a straight fashion, but slightly sideways. Consequently, in the present embodiment, the annular cushion 20 is adjoined to a lateral part of the head part 14, which lateral part faces in a direction at least partly parallel with the plane of the laryngeal opening 11.

Therefore, the lateral part of the head part faces at least partly in a parallel direction with the plane of the laryngeal opening 11. The laryngeal opening plane side of a head part (i.e. the side which does not even partly face in a parallel direction with the plane of the laryngeal opening) is called the bottom side or the bottom of the head part (i.e. the bottom of the mask itself).

In such embodiments it is especially advantageous to connect the annular cushion in a way shown in FIGS. 2, 3, 4 and 5 by two parallel circumferential adherings 26a, 26b or by two welding lines arranged similarly (i.e. in summary, along two parallel circumferential connection lines) to the head part 14, because the force acting on the back-folded (e.g. folded on the laryngeal opening 11) annular cushion 20 as a result of its inflation (due to the air introduced into the annular cushion 20, it goes into its inflated shape) pushes the annular cushion 20 outwards due to the arrangement of the connection lines, and hence it can easily occupy its final position (it is forced outwards from the folded back position) and remain in this place. To this end, therefore, in the present embodiment, the annular cushion 20 is adjoined to the head part 14 along two parallel circumferential connection lines (for example by adhering applied in strips or by welding along lines).

This outwards forcing effect is manifested especially advantageously, if the annular cushion is connected to an edge of the head part, as in the embodiment of FIG. 1. However, the effect which entails forcing outwards and keeping in place arises because of applying two parallel circumferential connection lines, i.e. this effect arises even when the annular cushion is connected like this (by two connection lines), but not to the end part of an edge.

Numerous configurations are conceivable, where the annular cushion is connected to a lateral part meeting such a definition. There are also such laryngeal mask head parts, the lateral wall of which includes an angle of 90° with the bottom surrounding the laryngeal opening, and in this case the lateral part—to which the annular cushion is connected—not only partly, but also fully faces a direction parallel with the plane of the laryngeal opening. The present embodiment of the invention is advantageous, because in case the annular cushion is adjoined to the lateral part of the head part, the lateral size (effective head size) of the laryngeal mask can be greatly decreased by arranging the covering element according to the invention. As already shown in the introductory part of this application, in case the annular cushion is arranged laterally, the applied head part has smaller lateral dimensions than such a head part, where the annular cushion is connected to the bottom part, because the anatomic environment determines the size of the annular cushion and not that of the head part. The size of the head part is depends on that the annular cushion is connected to the bottom or side of the head part.

According to the invention, therefore, the annular cushion can be connected also to the bottom or lateral part of the head part. In a case of the invention when the annular cushion is connected to the bottom of the head part, the height of the laryngeal mask is substantially reduced by the application of the covering element (in case the covering element or its appropriate part has not been removed yet). If the covering element is applied, the annular cushion does not stand free, and therefore nothing can be caught in it (e.g. a tooth or the epiglottis) while being driven to its application position. If the annular cushion is fixed to the side of the head part, a head part of smaller lateral size is to be applied in the laryngeal mask in comparison with the head part of a mask, where the annular cushion is arranged on its bottom side (cf. FIGS. 15A and 15B of US 2003/0037790 A1). If the annular cushion extends to the bottom and also laterally (the head part portion applied for its fixing faces downwards and also sideways), then of course the lateral size and height of the given laryngeal mask can be simultaneously reduced by applying the covering element. Therefore, preferably, a head part having the smallest possible lateral dimensions can be applied when the annular cushion is laterally arranged.

The following advantages of a laryngeal mask according to the invention are obtained in all embodiments.

When the covering element is applied, the bottom of the laryngeal mask according to the invention has a homogenous and flat and smooth surface, and therefore it can be easily slipped to its application position; this configuration ensures an easier movement in the anatomic space (oral cavity, tongue, esophagus-trache common section). Due to the arrangement of the covering element according to the invention, the annular cushion does not therefore protrude while the laryngeal mask is inserted into the patient, and it does not get caught in the objects (teeth, epiglottis) existing in the anatomic environment. It is a further advantage that the material of the annular cushion can be selected according to the expectations arising at the application position, for example, it is not necessary to apply an annular cushion of relatively large thickness which resists damage by teeth. While inserting, the annular cushion is protected from damage by the covering element (it is sufficient if the covering element has a thickness meeting this requirement, it is not necessary to make the annular cushion also from a thick resistant material).

It is a further common advantage that in the case of a laryngeal mask having a configuration according to the invention, more space remains free and visible in the oral cavity for physician (compared to known approaches), and hence for the physician it is easier to position the mask on the tongue, which is the initial position of inserting the mask, and then to drive the mask to its application position from the appropriate initial position.

The annular cushion of known laryngeal masks is only sterile until the moment it is placed into the oral cavity; when a known mask proceeds in the oral cavity which is an environment extremely rich in bacteria (various food morsels and foreign materials may remain in the oral cavity and in the teeth), its annular cushion loses its sterility when it is exposed to this environment. Accordingly, the annular cushion of the known masks reaches the entrance of the trachea as not being sterile and may carry foreign materials. On the contrary, according to the description above, in the case of this invention, the annular cushion does not carry contaminations with it, even its completely sterility may be provided until the covering element is removed in the application position of the laryngeal mask (when it is laid on the trachea), that is, because the annular cushion is not exposed (does not stand free), it is not able to carry pathogens with it, for example, from the oral cavity.

The smooth and flat part of the covering element 10 stretched on the head part 14 is preferably arranged in parallel with the plane determined by the laryngeal opening.

In the illustrated embodiments of the laryngeal mask, in its inflated state, the annular cushion has a circular cross section having annular cushion radius. The cross section of the inflated annular cushion is not necessarily a circle (see, for example, FIG. 6 of US 2003/0037790 A1; by way of example such a head part can be applied according to the invention where the connection of the annular cushion is arranged according to this figure).

In certain embodiments of the invention, a circumferential recess being formed to match the annular cushion radius is formed in the head part 14 for supporting the annular cushion at its part connected to the head part in the inflated state of the annular cushion. The head part is generally made of a material harder than the annular cushion, and therefore it is able to support the annular cushion.

In the embodiments shown in FIGS. 2, 5 and 6, the circumferential recess is formed on end part of edges 29, 28 and 32 in the head part 14. The recess is well visible also in FIG. 9 which shows a magnification. The circle corresponds to the section of the recess according to the figure is illustrated in FIGS. 2 and 5; this circle is identical with the circle of the appropriate cross section of the inflated annular cushion. This is how it is meant, that the recess is formed to match the annular cushion radius. The configuration of the circumferential recess allows an even more precise positioning of the annular cushion 20, i.e. the determination of the angle at which the annular cushion 20 is positioned after its inflation in relation to the head part 14. This angle can be interpreted in relation to the laryngeal plane determined by the laryngeal opening 11, and FIGS. 2 and 5 actually show those alpha and beta angles which are associated with the incidence angle of the annular cushion. This angle is included in a given section by a radius originating from the centre point (centreline) of the connection of the annular cushion 20 and the head part 14, and the extension of the laryngeal plane, in their intersection according to FIGS. 2 and 5.

It can be seen that in the case of FIG. 2, the recess is formed in a way that this angle is relatively small (the recess is formed substantially symmetrically in the end part of the edge). In the embodiment shown in FIG. 5, however, this angle is larger; it is observable in the figure that the associated recess is asymmetrically formed on the end part of edge 28.

The recess may not only be formed at the end of an edge, but also on a larger contiguous surface (for example, when a type of head part shown in FIG. 3 of US 2003/0037790 A1 is applied in the invention, in its lateral part), but it is important that the recess has an appropriate radius, because in this case it is able to orient the inflated annular cushion. If certain parts of the head part also have an edge, and in this part the recess runs along the end part of the edge, the recess may be formed on a larger contiguous surface in other parts.

As a result of folding back the annular cushion, a part containing air is formed in the annular cushion opposite the connection of the annular cushion (when the conditions on the annular cushion are not near vacuum conditions). This amount of air is preferably introduced into the annular cushion already at the time of manufacture. The outer end of the air inlet passage 18 is generally closed with a valve, and hence if the valve is closed, no air can enter into or escape from the passage 18. Air maybe introduced also if an inflating device (e.g. a pump) is already connected at the end of the passage 18. Generally, the air is discharged loosely from the annular cushion; and therefore an air cushion (air bubble) is created. To prevent the creation of an air cushion, a near vacuum status should be established in the annular cushion, to suck the opposite walls to each other principally. If this is not done, an air cushion is created due to the air captured in the annular cushion in a deflated state.

In the case of FIGS. 2, 5 and 6, i.e. when the annular cushion 20 is connected in such a way that the part applied for connecting includes an angle with the laryngeal plane, the part filled with air is formed opposite the end part of the edge due to the folding back of the annular cushion 20 with the covering element 10. In this case, the part filled with air runs all around (it is circumferential) the head part and functions as a kind of bumper element during the insertion of this embodiment of the laryngeal mask, because there is a part filled with air also in the front part of the mask (which is foremost when inserting the mask). Therefore, the configuration in which the annular cushion is connected to the lateral part of the head part has a further advantage, namely that in the course of inserting the mask, when the laryngeal mask would bump into an object in the environment, this part meets a soft 'air cushion', thereby further reducing the risk of injury. Hence, an appropriately arranged 'air cushion' layout is obtained, when the annular cushion is fixed to the side of the head part, as shown in FIGS. 1 to 6.

In this arrangement, the dimensions of the head part of the laryngeal mask before it is opened, i.e. when the part of the covering element to be removed is still connected with the releasable connection to the head part (directly or through the remaining part of the covering element) are only increased by the annular cushion with an extent equal to the bulging in relation to the head part in the folded back position. Compared to the size of the head part, this is a negligible increment (cf. for example FIG. 2: the increment is determined by the wall thickness of the annular cushion; substantially the increment is equal to twice the wall thickness due to the folding back). Accordingly, this very slight increase in size does not entail any disadvantage, in fact quite the opposite, because due to the folding back an 'air cushion' is preferably created all around the head part according to the description above. On the contrary, with the configuration according to the invention a very large decrease in the height and width of the mask is realized. If the annular cushion is fixed to the bottom side of the head part, it is conceivable that with the folding back of the head part even such an extent of lateral increase in size fails to take place.

FIGS. 2 and 3 are magnified views of the two encircled parts in FIG. 1. The part shown in FIG. 2 is a section of the passage 18 leading into the annular cushion 20. And, FIG. 3 illustrates the front part of the head part 14, which is foremost when the laryngeal mask is inserted into the patient. These figures show very well the manner of fixing the covering element 10 to the head part 14 in the present embodiment: the covering element 10 bypasses the folded back annular cushion 20, and is adhered circumferentially with the adhesive layer 24 to the edge 29 and to the edge 28, respectively, of the head part 14.

In the embodiment detailed above, the covering element 10 is adhered to the head part 14 by means of the adhesive layer 24. The fixing of the covering element to the head part may of course be carried out in other ways according to the description above, for example by baking or ultrasonic welding (when the covering element is baked or welded onto the head part), and especially preferably through the use of ultrasonic welding which does not require the addition of an auxiliary material. By means of these fixing types, a technical effect equivalent to that of adhering may be achieved, and furthermore these fixing types can be illustrated in the same way as the adhering in FIGS. 2, 3, 5 and 6, and therefore in the embodiments above, adhering can be easily replaced by these fixing types.

Hence, in the laryngeal mask according to the invention, a releasable connection is formed at the connection of the head part and the covering element or within the covering element. In the present embodiment, the releasable connection is installed in the covering element 10 by means of a thinning 22. As shown in FIGS. 2 and 3 (and as a magnification in FIG. 4), the thinning 22 runs (extends) all around the head part of the laryngeal mask. By arranging the thinning 22 according to the figures, a sufficiently large part of the covering element 10 can be removed by pulling out the puller element 12.

In the embodiment of FIG. 1 (as shown in the following figures), when the covering element 10 is removed by the puller element 12, a part of the covering element remains on the head part 14 of the laryngeal mask. FIG. 4 accordingly shows covering element parts 10a and 10b. When the puller element is pulled out, the covering element part 10a is removed and the covering element part 10b remains in its place (on the head part 14); accordingly, the puller element 12 is of course connected to the covering element part 10a of the covering element 10 to be removed, which is surrounded by the releasable connection.

In the present embodiment, a connection centreline is associated with the connection of the head part 14 and the annular cushion 20, with the intersection points of the covering element 10 and lines being perpendicular to the head part, starting from each point of the connection centreline, an inner covering element part extending above the laryngeal opening 11 and a peripheral covering element part located around the inner covering element part are defined (i.e. the intersection line created by the intersections divide the covering element into an inner covering element part and a peripheral covering element part; this is just a theoretical division, there is no such physical separation line as the releasable connection which connects the covering element parts 10a and 10b), and the releasable connection is formed circumferentially in the peripheral covering element part.

The annular cushion may be connected to the head part in a number of different ways (for example, in the illustrated embodiment, the fixing is provided by means of the adherings 26a, 26b) and in each case a connection centreline associated with the connection can be defined. In the illustrated embodiments, the connection is provided along the two lines defined by the adherings 26a, 26b, and similarly the annular cushion is connected to the head part along two lines according to FIG. 6 of US 2003/0037790 A1; in these cases the connection centreline is located between these connection lines, at an equal distance therefrom. In the case of connecting along a single line, the connection centreline is the connection line itself. Indeed, in the case of a different connection, the connection centreline can be defined similarly.

So then, perpendicular straight lines can be set up in each point of the connection centreline. If a circumferential recess is applied, these perpendicular straight lines are exactly in the radial direction (as shown in FIGS. 2 and 5). If no recess is applied, even then the straight lines are perpendicular to the surface of the head part in certain points of the connection centreline. As shown also in FIGS. 2 and 5, from the intersections of these perpendicular straight lines and the covering element 10 the releasable connection formed as the thinning 22 is positioned externally, i.e. towards the inlet tube, in other words towards the connection of the covering element 10 and the head part. If the releasable connection were within the intersection line obtained by the intersections, it would extend beyond the 'peak' obtained by folding in the annular cushion 20 (i.e. beyond the outermost point of the folded back annular cushion) and would retain the folded back annular cushion with its protruding edge, then after the removal of the appropriate part of the covering element, when the annular cushion is inflated, the annular cushion would have to be pushed over this edge, and the annular cushion could only be driven to application position by overcoming the resistance of the remaining covering element part (collar)—i.e. by tilting it through—(in such embodiments this is facilitated by a radial perforation shown in FIG. 29, which is an exemplary realization of the releasable connection line).

According to the present embodiment, the covering element part 10b remaining in its place does not hinder or bother at all the inflation of the annular cushion 20, because this remaining covering element part 10b will easily fold back when the annular cushion 20 is inflated (it is not stretched thereon).

Figure 28:
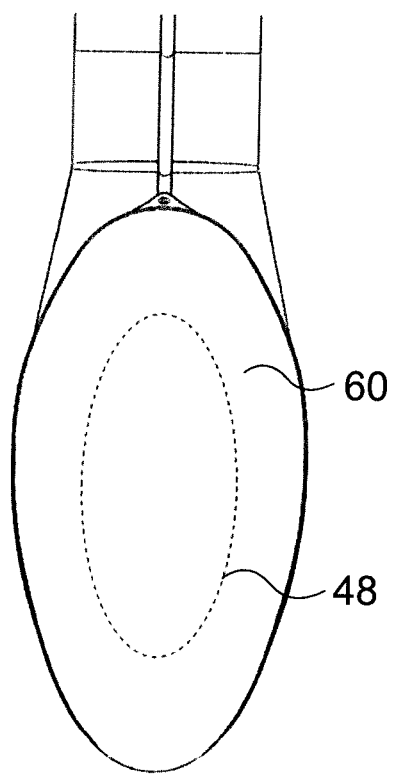
FIG. 28 shows in an embodiment the arrangement of the releasable connection on the covering element of the laryngeal mask according to the invention.
Figure 29:
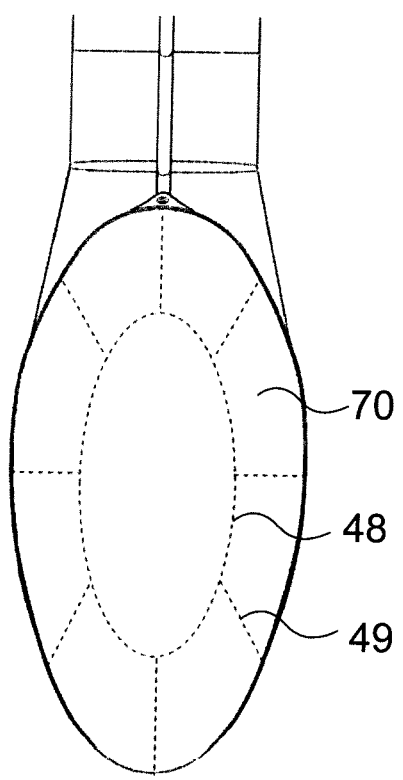
FIG. 29 shows in a further embodiment the arrangement of the releasable connection on the covering element of the laryngeal mask according to the invention.

If the releasable connection is arranged as described above, this leads to the fact that in order to remove the covering element part 10a of the covering element 10 by the puller element 12, a larger force is required to be applied than in case the releasable connection would be arranged closer to the centre of the laryngeal opening 11 (to the central part of the covering element 10). Such arrangement closer to the centre of the laryngeal opening is illustrated in FIGS. 28 and 29.

It is noted that the releasable connection could be arranged also at the connection of the head part 14 and the covering element 10. In this case the adhesive layer 24 should be designed and implemented in a way that when the puller element 12 is pulled with an appropriate force, it can be released. In this case, of course, it is not necessary to arrange the thinning 22 (naturally, it is sufficient to form only one instance of the releasable connection in order to be the removal of the covering element plannable).

FIG. 6 shows the arrangement of an annular cushion 30, which is thinner than the annular cushion 20 of FIGS. 1 to 5. In the case of known laryngeal masks currently available on the market, a 0.4 mm thickness of the annular cushion is considered to be thin. According to the discussion above, by the application of the covering element, the thickness of the annular cushion can be reduced well below this value (to the thickness actually required by the purpose of the laryngeal mask). By the application of a covering element of appropriate thickness, a very thin annular cushion may also be protected during insertion, and it is not disadvantageous to apply a covering element of appropriate thickness, because it does not have a function any more in the application position (wherefrom it is removed), and even the thickness of a covering element which is considered to be very thick is negligible compared to the dimensions of the head part. Accordingly, the thickness of the annular cushion can be selected expressly in accordance with the anatomic environment of the application position.

FIG. 6 illustrates a further advantage of the laryngeal mask according to the invention. In the case of known laryngeal masks, the material and thickness of the annular cushion were not determined by the preferences prevailing in the final anatomic position (when the mask reaches its application position on the top of the trachea). When selecting the material of the annular cushion from an anatomic respect, it is preferred if the configuration is as much atraumatic as possible, in order to avoid injuries and to ensure as tight a fit as possible. On the contrary, the known annular cushions (balloons) met the requirement that they were not damaged by external impacts (broken and sharp teeth, biting), until the mask reached its application position. Accordingly, the balloon of known masks was made from a coarser and thicker material.

On the contrary, in the case of the laryngeal mask according to the invention, it is possible to apply a thin and smooth material with a thickness corresponding to the anatomic space of the application position, i.e. it is not necessary to apply an excessively thick material in the annular cushion to make sure that it is not damaged during insertion, since the covering element protects the material of the annular cushion during insertion.

FIG. 7 is a perspective view of the embodiment of FIGS. 1 to 4. FIG. 7 illustrates the arrangement of the covering element 10 on the head part 14, with the puller element 12 protruding from the inlet tube 16.

The covering element and puller element according to the invention can be applied also in the case of laryngeal masks that have a configuration other than that illustrated, and accordingly also in masks where the annular cushion is fixed to the bottom part of the head part or also in the case of laryngeal masks having a head part of a configuration other than that illustrated.

When a head part of such a type (as for example shown in FIGS. 4A to 4C of US 2003/0037790 A1) is used in the laryngeal mask according to the invention where the annular cushion is fixed to the bottom part of the head part, the covering element according to the invention is also arranged around (surrounds) the annular cushion folded under the head, and it can be fixed on one part of the head part which is towards the inlet tube from the connection of the annular cushion. In case of such a configuration, the puller element can be connected to the covering element just like in the embodiment shown by FIGS. 1 to 4, because the puller element can be connected to the centre of the covering element, then guided between the folded back annular cushion parts, and then out through the inlet tube. The covering element can be fixed in a similar way also in these embodiments to the head part as in the embodiment shown in FIGS. 1 to 4 (with an adhesive layer to the lateral part of the head part) or in any other way around the head part.

Similarly, the solution according to the invention can also be applied in the case of such a head part design which is shown in FIG. 3 of US 2003/0037790 A1. In this case the fixing of the covering element to the front part of the head part could be done in a similar way as in the case of the embodiments shown in FIGS. 1 to 7, but it would be fixed in the rear part of the head part to the outer part of the practically vertical head part wall, a bit further than the annular cushion connection.

In both cases (and also in other similar cases) therefore, the covering element according to the invention can be arranged in the case of known head parts. In the other two cases described above, two extreme cases are demonstrated, in the first case the annular cushion bulges below the head (head part) (because it is mounted below the head), and in the second alternative the annular cushion is fixed to the side of the head, and therefore during use, the inflated annular cushion is disposed around the head. The approach of the invention can of course be applied in the case of configurations between these.

Let us return to the details shown in FIG. 2, where it is demonstrated how the covering element is fixed to the head part in the embodiment illustrated by FIGS. 1 to 4. Such a mounting solution is demonstrated here, where the covering element is connected by adhering to a certain surface of the head part (overlapping surface mounting). The overlapping mounting can be applied also in a part of the head part which is further towards the inlet tube, and therefore on the rear part of the head part 14 as shown in FIG. 2, the covering element can be connected also to the horizontal section of the head part as shown in the figure. For example, the fixing of the outer edge of the covering element along the line (by adhering or ultrasonic welding) is conceivable and there can be other solutions, too, for executing the mounting in such cases.

If the releasable connection is not located at the connection of the covering element and the head part, the exact manner of mounting is not relevant from the aspect of the invention. This is because the releasable connection is arranged on the covering element in this case, and the covering element part fixed to the head part remains on the head part anyway even after the other parts of the covering element have been removed. It is also clear that the releasable connection installed at the point where the covering element is connected to the head part can be formed in other ways, even by the alternative methods demonstrated above, by applying such a adhering or ultrasonic welded connection which is released in case a certain force is applied.

Therefore, in such an embodiment of the invention where the releasable connection is formed at the connection of the head part and the covering element, it is not necessary to use a further releasable connection in the covering element. A releasable connection can be formed therefore by way of example with an adhesive which is separated under a given pulling force, with an appropriately weakened adhering (for example, in such embodiments, where the connection of the covering element and the head part is not arranged all around (circumferentially) in such a way that a adhesive dot is applied at certain intervals) and also in other ways. Of course, it is not only the adhering (adherence) which can be weakened, but also a weakened connection (interrupted at certain points) can be formed by ultrasonic welding. Such a welding can be a welding with or without an auxiliary material. Accordingly, in such embodiments, the releasable connection is again formed circumferentially; in this case this means that the interruptions of the adhering, ultrasonic welding or other connections (i.e. the non-adhered and non-welded sections) are arranged in such proportions (density) along the full length of the releasable connection compared to the connected (e.g. welded, adhered) parts that all around (circumferentially) i.e. in the full length of the releasable connection it is ensured that the releasing (i.e. tearing) of the releasable connection can be planned and controlled. Depending on the pulling force applied, the accurate configuration of such a connection can be determined (i.e. the proportions of the lengths of the welded or adhered sections in relation to the non-welded or non-adhered sections arranged among them).

FIG. 1 shows the laryngeal mask according to the invention in a state when the removal of the covering element part 10a of the covering element 10 has not been started yet. The process of removing the covering element is shown by FIGS. 8, 10 and 12.

Figure 9:
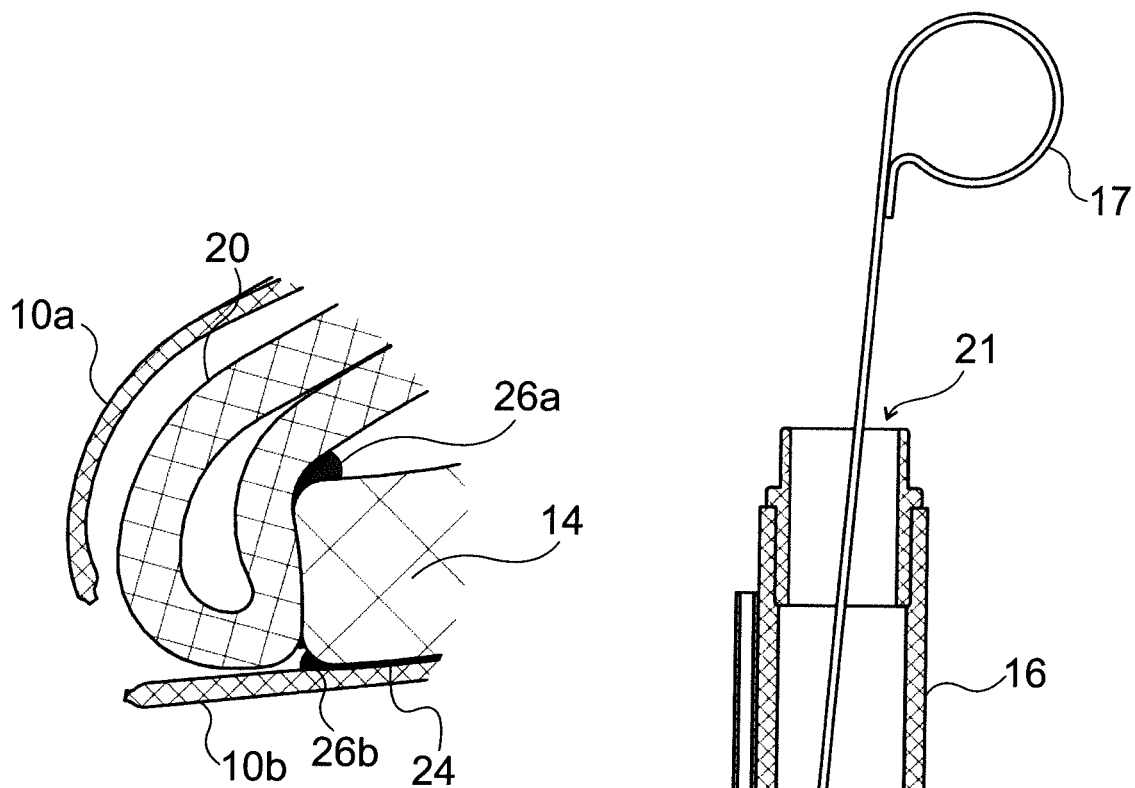
FIG. 9 is a magnified drawing of the part encircled in FIG. 8.
Figure 8:
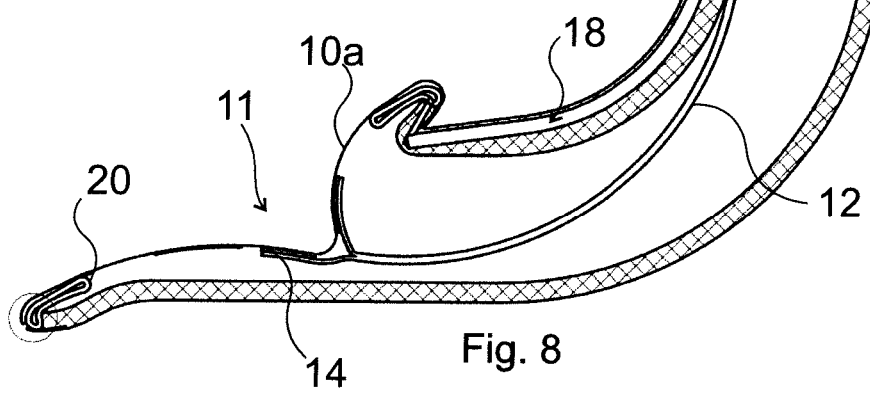
FIG. 8 shows the embodiment of the invention of FIG. 1 in such a status, when the removal of the appropriate part of the covering element has already been started.

The first step of the removal is illustrated in FIG. 8 or in FIG. 9 which shows a detail of FIG. 8. FIG. 8 shows that when the puller element 12 is pulled outwards, i.e. towards the open end (inlet opening) of the inlet tube 16, the covering element 10 can be pulled towards the inner part of the head part 14 (to the inner space of the inlet tube 16). The removal of the appropriate part of the covering element is preferably initiated by a continuous and uniform straining of the puller element, and due to this at a certain point the releasable connection starts to release (comes apart); by way of example the releasable connection designed as the thinning 22 cracks at a given point. Subsequently, as shown by the figures described below, preferably the separated part of the covering element is completely removed by from the passage of the laryngeal mask pulling it continuously. Finally, the annular cushion is inflated to an appropriate size. This latter step can of course be taken on the basis of the acceptably applied and learnt protocol of prior art masks.

FIG. 8 illustrates the time moment when the releasable connection formed as thinning 22 between the covering element parts 10a and 10b just about releases, i.e. releases at the front part of the head part 14 shown in FIG. 9. The releasing or releasing represents a planned and controlled tear along the thinning 22, if such a 22 thinning is used. Similarly, in the case of other types of releasable connections, plannability and control can also be achieved. FIG. 9 clearly shows that along the thinning the covering element parts 10a and 10b are separated, and when pulled further, the covering element part 10a is separated circumferentially from the covering element part 10b, and hence the covering element part 10a which is connected to the puller element 12 through the connecting feet 19 becomes removable. As illustrated not only in FIGS. 8 and 9, but also in FIGS. 20A to 20E, preferably only at one end (for example, at the front end) will the removal of the covering element part 10a of the covering element 10 be started; in the present embodiment, the covering element part 10a of the covering element 10 is removed. The accurate point of adjoining the covering element and the puller element, and the configuration of the advantageously applied connecting feet will determine where the separation would be initiated.

It is shown by FIG. 9 also that the covering element part 10b leans outwards; the covering element part 10b will not hinder the inflation of the annular cushion (does not influence its movement) as shown in FIG. 13. It is shown in FIG. 8 how the connection feet 19 of the puller element 12 pull the covering element 10. In a given case, the covering element 10 may also be elongated slightly before tearing along the thinning, but the puller element 12 and the elements contributing to the removal of the appropriate part of the covering element 10, i.e. the puller element 12, the connecting feet 19 and the covering element are made from such a material which appropriately tears along the thinning, and in addition it does not lengthen excessively, and therefore it will not hinder or impede the removal of the appropriate part of the covering element 10. Preferably, the materials of the covering element and the puller element are selected in a way that the elongation of the material is negligible during the pulling process. The material of the covering element according to the discussion above is by way of example PVC or its derivatives. FIG. 9 shows clearly the adherings 26a, 26b, and the adhering 24 which is applied in order to connect the covering element part 10b to the head part 14.

FIG. 10 shows the next step of removing the covering element part 10a, when the covering element part 10a has already collapsed at the end of the puller element 12 (it is shown as folded between the connecting feet 19 in the figure) and a large part of the puller element has already left the inlet tube 16. In this status, the annular cushions 20 may start to bulge, because they are no longer retained by the covering element 10. It depends on the choice of material how far they start to protrude in this phase from their folded position, but once inflated, they will occupy their application positions. It is, however, obvious that the annular cushions would only become exposed at this point in time, i.e. in the present embodiment the sterility of the annular cushion is preserved up to this moment (when the laryngeal mask is already driven to application position), i.e. the annular cushion is sterile when unfolded, and it is sterile in its inflated state when it reaches its application position.

Figure 14:
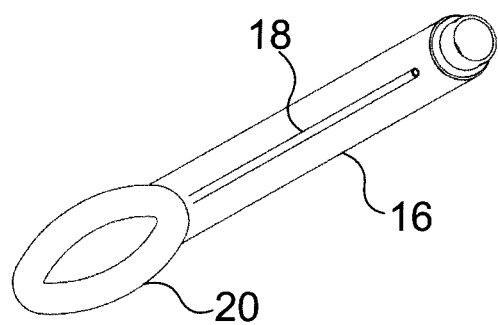
FIG. 14 shows the status of FIG. 10 in a bottom perspective view.

FIG. 14 also shows the laryngeal mask in the status of FIG. 10, i.e. at the time when the annular cushion 20 is still folded back. FIG. 14 shows the laryngeal mask from the direction of the annular cushion.

FIG. 11 shows a pull-out mechanism standing free, i.e. the puller element 12 with a loop 17 and the covering element part 10a which is to be removed and which is connected through the connecting feet 19 to the puller element 12. FIG. 11 shows the components the embodiment of FIG. 1 after the activation of the puller element, i.e. after the removal of the appropriate covering element part, and accordingly in the figure the covering element part 10a is connected to the puller element 12.

FIG. 12 shows such a state of the laryngeal mask, when the annular cushion 20 is already inflated, and the covering element part 10a has been completely removed from the laryngeal mask (i.e. after leaving the inlet tube 16). The inflation of the annular cushion 20 is carried out through the air inlet passages 18, when an appropriate inflating device (for example, a pump or a different known device suitable for inflation) is connected to the outer end of the passage 18.

FIG. 13 shows the encircled detail of FIG. 12, which illustrates the cross section of the inflated annular cushion 20, and also the folding back of the covering element part 10b along the inflated annular cushion 20 at the connection of the annular cushion and the head part 14. It is also shown in FIG. 13 how the annular cushion is located in relation to the edge of the head part 14. On the one hand, the annular cushion is held in place by the adherings (adhesive elements) 26a and 26b, and on the other, its position is determined also by the recess at the end part of the head part 14. In the figure, the recess at the end part of the head part 14 is only partly visible, and its arrangement is shown also by the fact that the annular cushion 20 fits the end part of the head part 14, and its circular cross section is not distorted there.

Figure 16:
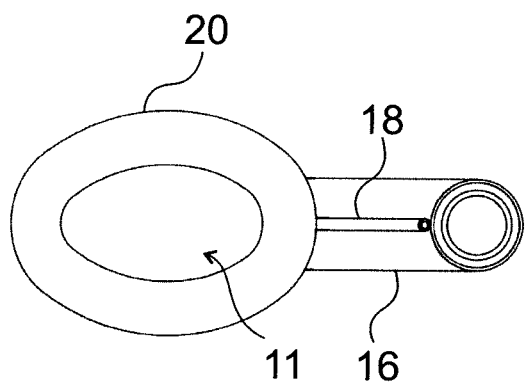
FIG. 16 is a perspective view of the laryngeal mask with inflated annular cushions in the status of FIG. 12.

FIG. 16 is a perspective view of the state of FIG. 12, viewed from the annular cushion 20. It can be seen by comparing FIGS. 14 and 16 that the actual head size of the laryngeal mask is greatly increased when the appropriate part of the covering element (or even the whole covering element) is removed and the annular cushion is inflated. When the annular cushion is still folded back to the head part of the laryngeal mask, the effective head size is greatly decreased. When, however, the annular cushion bulges around the head part, then the effective head size is greatly increased (i.e. the unfolding of the annular cushion increases the actual head size regarding length, width and—since in most cases the inflated annular cushion bulges also at the bottom in relation to the head part—mostly thickness). Because, however, in the case of the laryngeal mask according to the invention the covering element (i.e. its part to be removed) may stay on the head part until the laryngeal mask reaches its appropriate application position in the patient, the complete insertion process may be carried out with a small actual head size, i.e. during insertion the head part can be reduced to the smallest possible (anatomically determined) size that can be practically achieved.

As discussed above, the lateral extension of the head part in the present embodiment if the annular cushion is connected to the head part side is much smaller than that of the head part to which the annular cushion is connected from the bottom and which is disclosed by way of example in FIGS. 4A to 4C of US 2003/0037790 A1 (for a comparison, see FIGS. 15A and 15B of the document). This is because the anatomic environment determines the size of the annular cushion (and not the size of the head part), i.e. the size of the annular cushion in the case of a certain given patient anatomy has to be the same in the case of the invention and in the case of FIGS. 4A to 4C of US 2003/00378890 A1. Because, however, in the case of this known approach the annular cushion is connected to the head part from the bottom, the head part has to by all means be larger than in a case when the annular cushion is fixed to the side of the head part.

Therefore, the insertion can be performed with a much smaller actual head size than in the case of the approach of US 2003/0037790 A1, and furthermore by means of the covering element it is provided that the deflated annular cushion is not only simply folded under the head part, but it is sealed therein by means of the covering element.

Figure 15:
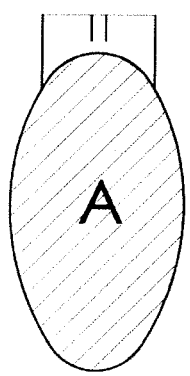
FIG. 15 is a schematic drawing illustrating the initial dimensions of the head part.
Figure 17:
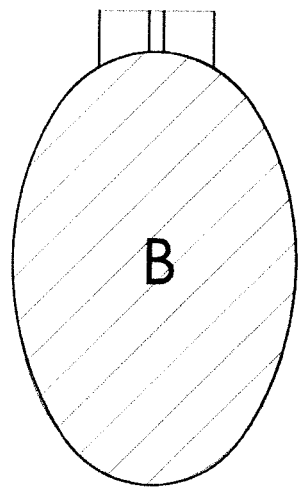
FIG. 17 is a schematic drawing illustrating the dimensions of the laryngeal mask head part and the connected inflated annular cushion.

FIGS. 15 and 17 show the comparison between the effective head part sizes, in the cases when the appropriate part of the covering element is still on the head part (FIG. 15) and in case when the appropriate part of the covering element has already been removed, and the annular cushion has been inflated (FIG. 17).

Figures 18, 19:
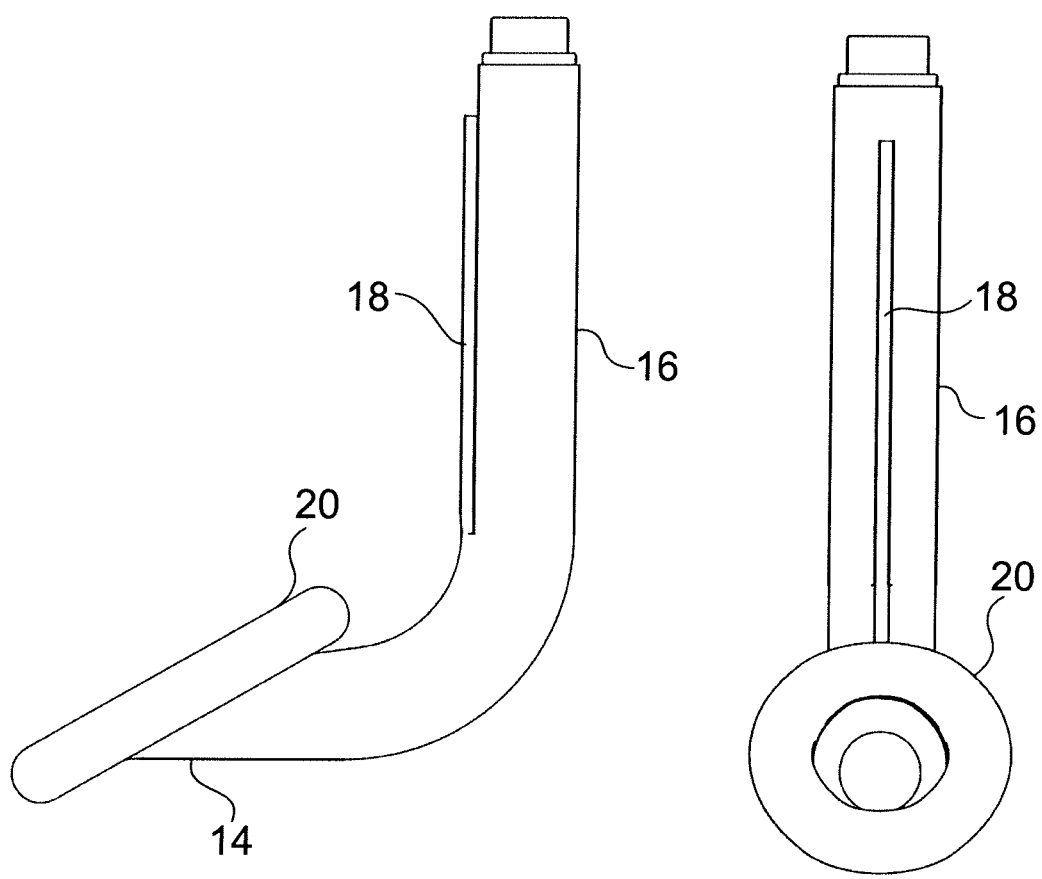
FIG. 18 is a side view of the laryngeal mask according to the invention with the annular cushion inflated.
FIG. 19 shows a status similar to that of FIG. 18 from the front.

In FIGS. 18 and 19, the final state of the laryngeal mask at its application position is shown, i.e. the side view and front view of the laryngeal mask are shown with the annular cushion inflated.

Figures 20A, 20B, 20C, 20D, 20E:
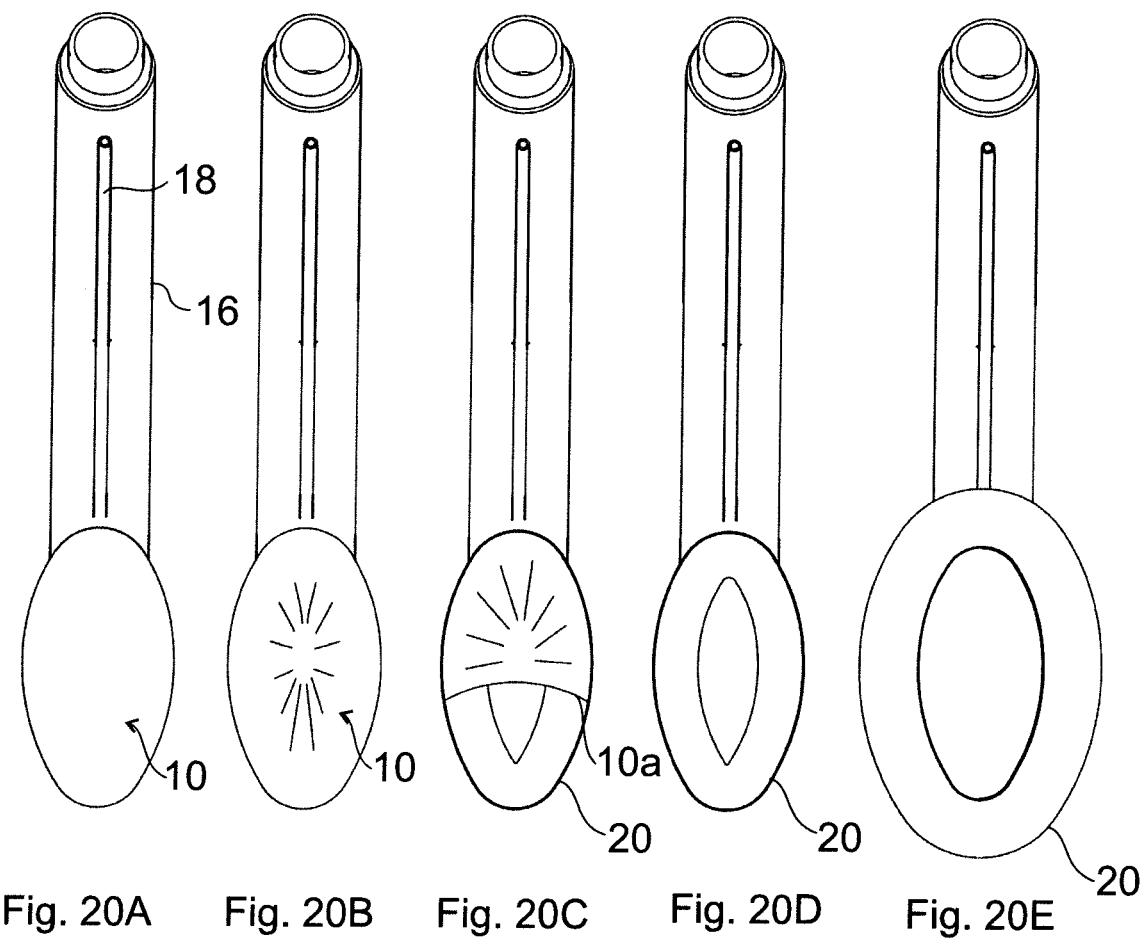
FIGS. 20A to 20E are front views of the appropriate part of the laryngeal mask covering element, illustrating the phases of removal.

FIGS. 20A to 20E are front views to show an exemplary process of removing the covering element part 10a as well as the inflation of the annular cushion 20. In FIG. 20A, the covering element 10 is still arranged on the laryngeal mask. FIG. 20B illustrates the state when the process of pulling out the puller element from the laryngeal mask has started. In this case the middle part of the covering element 10 is stretched and slightly pulled inwards. This is shown by the radial lining in the figure. FIG. 20C shows that on the front part of the laryngeal mask, the covering element part 10a has already been separated at the releasable connection from the covering element part 10b connected to the head part (the covering element part 10b is not shown in FIGS. 20A to 20E), but other peripheral parts of the covering element part 10a are still connected to the head part, and it is gradually separated along the releasable connection around the head part.

Figure 25:
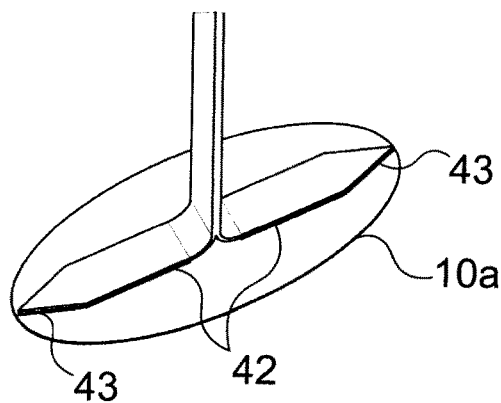
FIG. 25 is the view of FIG. 24 in a further embodiment.
Figure 26:
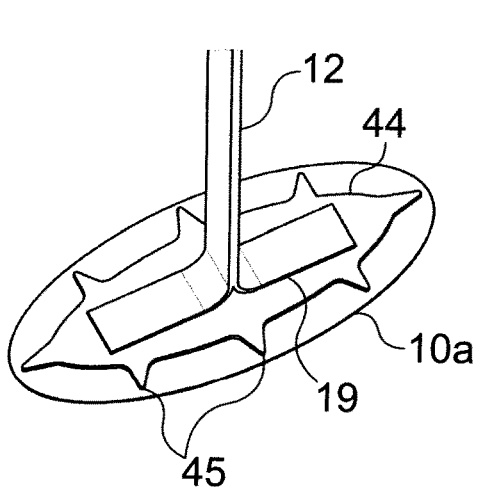
FIG. 26 is the view of FIG. 23 in a yet further embodiment.

The configuration of the releasable connection and connecting feet tunes exactly how the covering element part 10a is separated from the covering element part 10b connected to the head part. This is because the puller element and the connection of the connecting feet to the covering element 10 can be formed in a way that the covering element part 10a starts to separate at the front part from the covering element part 10b remaining on the head part, and the releasing of the releasable connection occurs gradually in case the puller element 12 is pulled further. To this end, first the pulling force has to be concentrated on the front part of the covering element where the releasing of the releasable connection is intended to be initiated. The further embodiments of the covering element and the puller element connection are shown in FIGS. 25 and 26. This will be described in details in association with the figures.

FIG. 20D shows the state when the covering element has already been removed, but the annular cushion 20 is not yet inflated. FIG. 20E shows the annular cushion in an inflated state.

Side views of the covering element removal process as illustrated in FIGS. 20A to 20E are shown in FIGS. 21A to 21E. FIG. 21B shows a better view of the covering element 10 as it is pulled inwards into the head part and FIG. 21C illustrates that the covering element part 10a of the covering element 10 has already been separated and its other parts are also pulled off the head part. FIG. 21D shows the annular cushion 20 still in a deflated state, and FIG. 21E shows the annular cushion 20 in an inflated state.

FIGS. 22A to 22E illustrate realization possibilities of the releasable connection according to the invention by way of example. In the embodiments of the invention corresponding to these figures, the releasable connection is formed in the covering 25 element, with one of the following:

a thinning,
a split perforation,
a hole line perforation,
a combination of thinning and split perforation,
a combination of thinning and hole line perforation.

When thinning is applied as a releasable connection, the uniform distribution along the thinning of the force applied for releasing the releasable connection is especially advantageously can be provided. A split perforation or a hole line perforation can be advantageously applied in that part of the releasable connection where the applied pulling force is concentrated in order to start the tearing (the releasing of the releasable connection).

It is a great advantage of these realizations of the releasable connection that they can be used to realize the releasable connection to be plannable (preferably the planned tearing of the covering element), i.e. they enable, for example, the planning and adjustment of the pulling force which releases the releasable connection, i.e. the force which makes the covering element separate/tear into a removed part and a part remaining on the head part.

The combination of thinning and split perforation or thinning and hole line perforation is described below, but the split perforation and the hole line perforation can also be combined in a way that in the areas adjoining the holes of the hole line, a split perforation is used, i.e. in an embodiment the perforations with splits and the hole line perforations will jointly (alternating with each other) form the releasable connection. For example, thinning can be applied advantageously in most of the length of the releasable connection, but—in order to facilitate the start of the tear—instead of or in addition to the thinning, a split perforation or hole line perforation can be applied advantageously at the end parts of the head part.

Figure 22A:
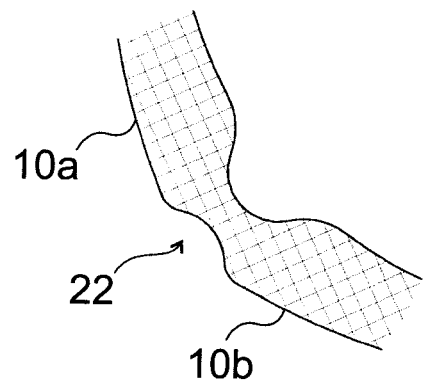

FIG. 22A illustrates the thinning 22 (weakening in the material of the covering element) arranged between the covering element parts 10a and 10b, and this was also shown in e.g. FIGS. 1 to 6.

Figure 22B:
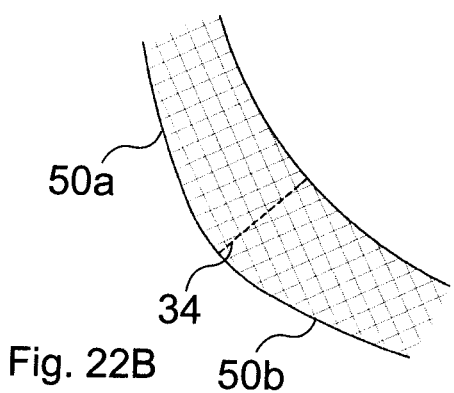
Figure 22C:
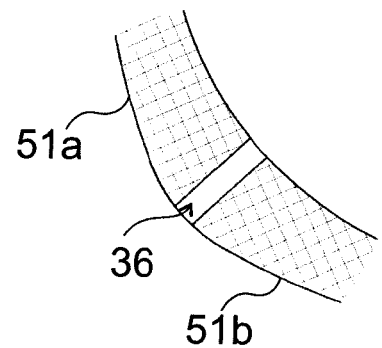

FIG. 22B shows a perforation 34 with splits between covering element parts 50a and 50b. In the case of split perforation, the covering element material is weakened without a loss of material, in order to form the releasable connection. FIG. 22C shows a weakening with loss of material, in which case the releasable connection is formed by means of hole line perforation 36 in the covering element, or more precisely between its covering element parts 51a and 51b. The cross section shown in FIG. 22C indeed goes through a hole (punching) of the hole line perforation 36. The strength of the releasable connection can be controlled by the spacing among, as well as the diameter of the holes.

Figure 22D:
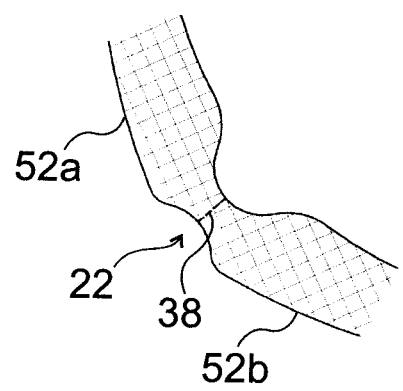
Figure 22E:
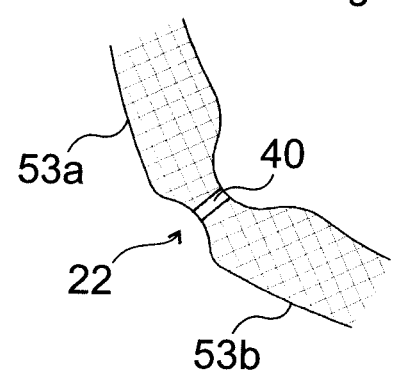

FIG. 22D shows one combination of the previous realizations of the releasable connection. In this case thinning 22 is also formed between covering element parts 52a and 52b, and in addition a perforation 38 with splits is formed in the centre of the thinning 22. FIG. 22E also shows such an embodiment of the releasable connection, which is a combination of the approaches above. In this embodiment, the thinning 22 is again formed between covering element parts 53a and 53b, and a hole line perforation 40 is also arranged in the thinning 22 with a hole array of appropriate periodicity. The cross section shown in FIG. 22E indeed goes through a hole of the hole line perforation 40.

Figure 23:
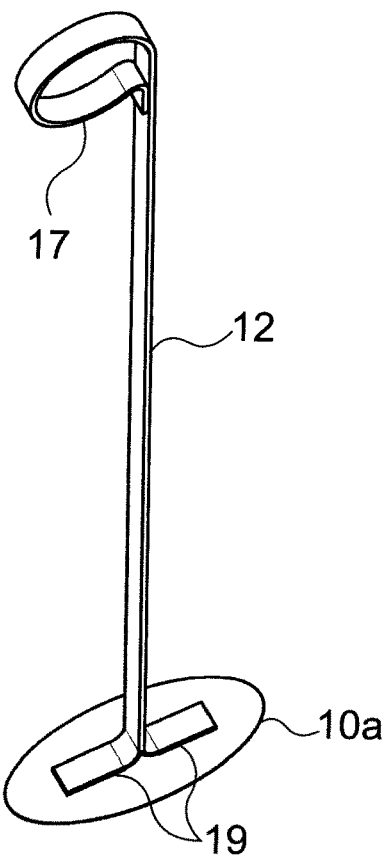
FIG. 23 is a further view of the puller element shown in FIG. 11.
Figure 24:
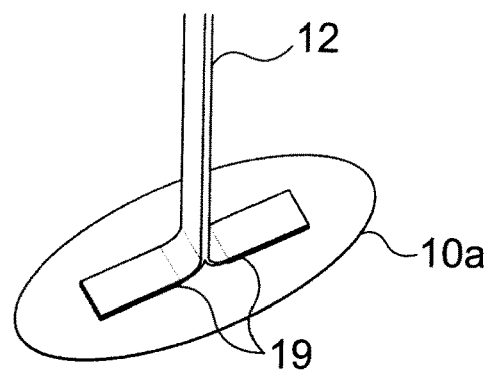
FIG. 24 is a magnified drawing of one detail of FIG. 23.

FIG. 23 is a different view of the component shown in FIG. 11. A part of FIG. 23 is shown magnified in FIG. 24. This shows the connection of the covering element part 10a and the connecting feet 19.

This part is also illustrated in the magnification of FIGS. 25 and 26, but in these embodiments, the type of connection of the puller element 12 to the covering element part 10a is different.

A connecting foot 42 is arranged in the embodiment of FIG. 25. In this embodiment, the connecting feet 42 each have a tip 43 substantially reaching the releasable connection and narrowing towards their end part, i.e. both connecting feet 42 ends protruding outwards are narrowing in a triangular shape. The connecting feet 42 are elongated in comparison with the connecting feet 19 in the direction of head part ends, and the tip reaches the releasable connection. In light of the fact that the releasable connection is implemented e.g. with a thinning, the definition that the tip practically reaches the releasable connection means that it comes very close (approx. 0-5 mm) to it (for example, this is how close it gets to the part where the thinning starts). FIG. 25 shows the removed part of the covering element 10 (covering element part 10a), i.e. the part which has already been separated from the head part at the releasable connection; accordingly, the figure shows that the tip 43 reaches the releasable connection.

By applying the connecting feet 42 with the tip 43, the pulling force can be concentrated even better towards the head part and hence towards the end part of the covering element than in case of the embodiment comprising the connecting feet 19, and therefore the present embodiment is even more efficient in providing that the tearing of the releasable connection starts at one end of the head part.

In an embodiment of the invention, the puller element is connected to the covering element through an oval base part having radial protruding parts. Such an embodiment is shown in FIG. 26. In the present embodiment, the connection through the oval base part having radial protruding parts is implemented in a way that the connecting feet 19 have an oval base part and radial protruding parts 45 (which also preferably substantially reach the releasable connection) connected to a connection insert 44, and the connection insert 44 is connected to the removable covering element part 10a (located within the releasable connection) of the covering element 10. The connection insert 44 is fixed to the inner side, i.e. the inlet tube facing side of the covering element 10, and the connecting feet 19 are connected to this connection insert 44. The configuration of the connection insert according to FIG. 26 facilitates starting the releasing of the releasable connection simultaneously at several points. Connection via the oval base having radial protruding parts may also be implemented in a way that the connecting feet themselves have an oval base and parts protruding in a radial direction, and in this case it is not necessary to use the connection insert. By means of this approach, the pulling force can be moved along the releasable connection uniformly and as planned.

Of course, a number of protruding parts deviating from that illustrated in the figure may also be utilised. It is also conceivable that certain protruding parts approach the releasable connection further than others, and it is also conceivable that the protruding parts have different dimensions. Accordingly, a connecting foot with such a base part is conceivable, which has a single long protrusion in the direction of one end (like the tip 42 shown in FIG. 25), and which has a similar configuration in the direction of the other end as the connection insert 44 in FIG. 26 (of course, only half of it) with a different number of protruding parts.

Figure 27:
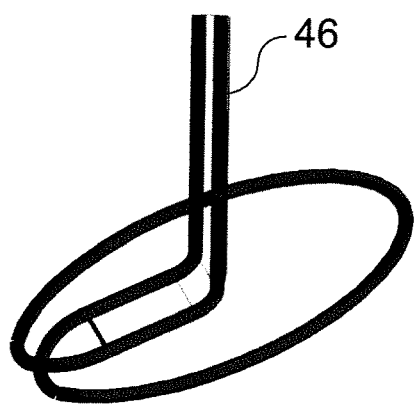
FIG. 27 is a perspective view illustrating a strengthening yarn which can be integrated into the puller element and the covering element.

The invention comprises in an embodiment a strengthening yarn 46 (shown in FIG. 27) made from one piece, arranged longitudinally in the puller element and circumferentially in the covering element between the connection of the puller element and the releasable connection. This strengthening yarn 46 can be guided all along in the configuration of the figure, and it is integrated into the puller element and the covering element. By means of this strengthening yarn 46, the integrity of the unit consisting of the puller element and the covering element can be enhanced, i.e. the tearing of this unit can be avoided even more efficiently using the strengthening yarn 46, and furthermore the distribution of the pulling force and the tearing (releasing) can be controlled even more advantageously. The strengthening yarn is made of kevlar (poly-paraphenylene terephthalamide)) by way of example.

The connection of the puller element to the inner side of the covering element may also be implemented according to the invention in a way that the covering element and the puller element are made from one piece. In this case the strengthening yarn 46 can be especially advantageously applied.

FIG. 28 shows a further embodiment of the releasable connection comprising a covering element 60. In the present embodiment, a connection centreline is associated with the connection of the head part 14 and the annular cushion 20, with the intersection points of the covering element 60 and lines being perpendicular to the head part and starting from each point of the connection centreline, an inner covering element part extending above the laryngeal opening and a peripheral covering element part located around the inner covering element part are defined (the line of the intersections divide the covering element into an inner covering element part and a peripheral covering element part), and the releasable connection is formed circumferentially in the inner covering element part. When the releasable connection is arranged in such a way, advantageously a smaller pulling force is to be applied than in the embodiments shown in FIGS. 1 to 7.

Therefore, in the case of FIG. 28, a perforation 48 is located in a more inner part of the covering element 60 (the releasable connection is implemented with the perforation 48), i.e. only an inner part of the covering element 60 surrounded by the perforation 48 can be removed by means of the puller element. In this case, in comparison with the embodiments above, a large covering element part remains on the head part, but the annular cushion is able to fold out this covering element part also during inflation, and as a result of inflation, it is able to find its way out from under it.

To facilitate folding out this relatively large remaining covering element part, a covering element 70 is applied in the embodiment of the invention shown in FIG. 29. Additional releasable connection lines extending outwards from the releasable connection and from a central part of the covering element 70 are formed in the covering element 70. The releasable connection lines are implemented with perforations 49 in the embodiment of FIG. 29, but the releasable connection lines may also be implemented as the releasable connection, i.e. by way of example as the approaches shown in FIGS. 22A to 22E. The part of the covering element 70 remaining on the head part may be torn along the perforations 49, thereby facilitating the folding back of the covering element parts.

Such radial perforations may be applied also in the embodiments shown in FIGS. 1 to 7, because when they are used, the remaining covering element part 10b remaining there is also able to tear. However, if the remaining covering element part has appropriately small sizes, the application of such perforations is not necessary.

Figure 30:
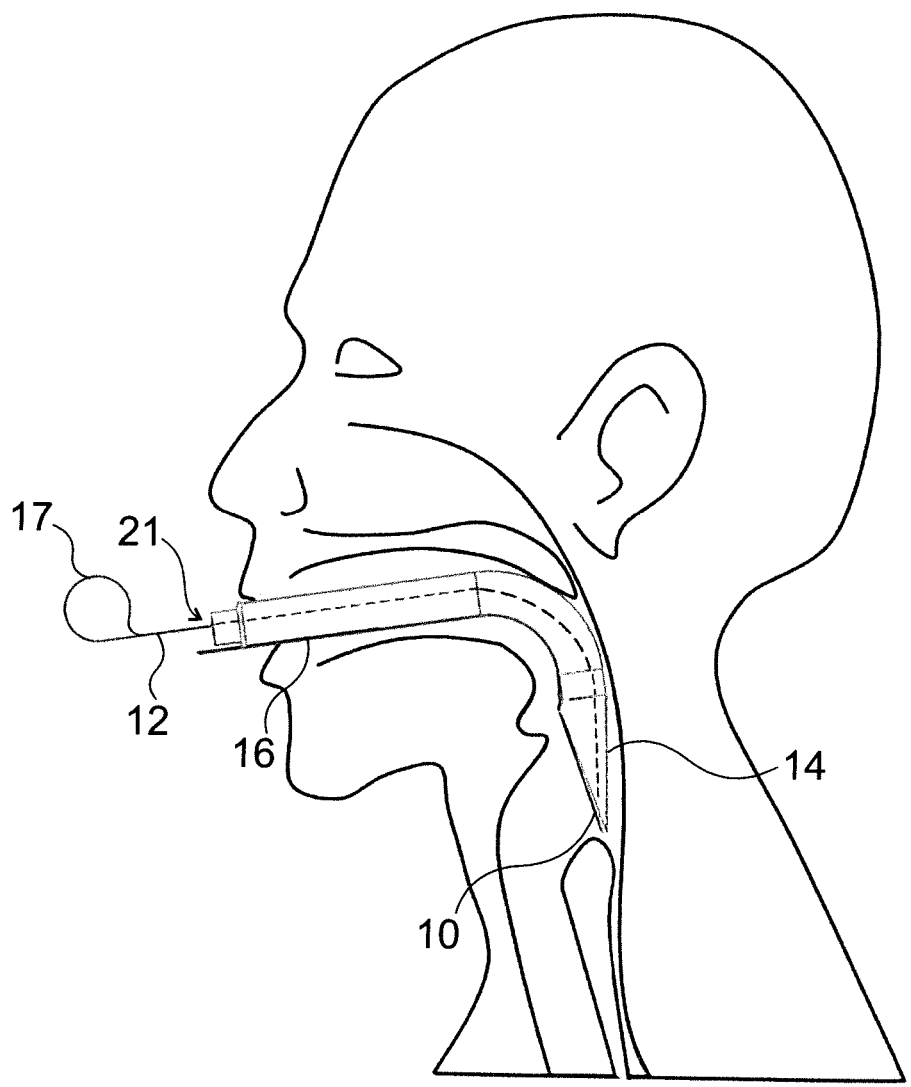
FIG. 30 illustrates the method of inserting a laryngeal mask according to the invention in such a phase of insertion, wherein the laryngeal mask is already in its final application position, but the annular cushion is still in the space sealed by the covering element.
Figure 31:
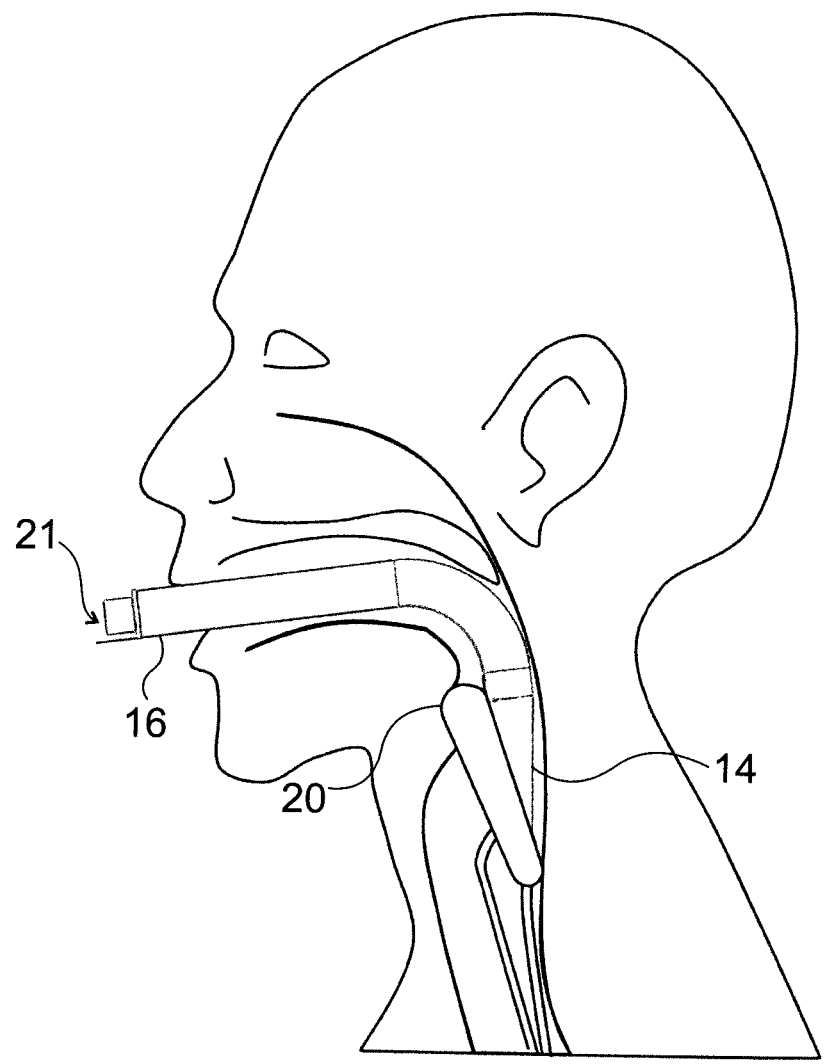
FIG. 31 shows the arrangement of the laryngeal mask in a place identical with that of FIG. 30, but with the annular cushions already released.

FIGS. 30 and 31 illustrate the insertion of the laryngeal mask according to the invention into the patient. FIG. 30 shows the state when the covering element protected (covered) laryngeal mask according to the invention is driven to its application position, i.e. to the outlet of the trachea. It is shown that in comparison with the anatomic environment, the size of the head part is small (the annular cushion does not protrude from it either downwards or laterally) and hence the laryngeal mask according to the invention can be easily driven to the application position. FIG. 31 shows the state when the annular cushion 20 is already opened. It is shown that in this case the annular cushion bulges above the end of the trachea, similarly to the generally used laryngeal masks. By removing one part or the whole of the covering element therefore the deflated annular cushion 20 emerges, and after inflation it is introduced to the position shown in FIG. 31. Inflation is carried out similarly to known approaches, because even in those approaches the annular cushion is deflated in the beginning.

By removing one part or the whole of the covering element, the passage of the laryngeal mask becomes free through the laryngeal opening. Similarly to known devices, a respirator is only connected to the inlet opening of the inlet tube once the annular cushion has been inflated. At this moment the puller element together with the appropriate part of the covering element have already been removed from the passage ending in the inlet opening.

The dimensions of the laryngeal mask to be applied are determined by the body measurements of the patient; the known laryngeal masks are generally available in 5 to 7 different sizes (from infant size to adult size). The dimensioning of the mask also determines the dimensioning of the annular cushion, i.e. it is required to utilise an annular cushion characterised by various sizes of cross sections in the case of a child or an adult (in accordance with the application position assumed in the inserted position, the anatomic environment determines the dimensions of the annular cushion to be applied, and the dimensions of the head part change depending on the part of the head part the annular cushion is connected to). In the case of an adult, the radius of the cross section of an annular cushion with circular cross section is approx. 1 cm.

The invention is, of course, not limited to the preferred embodiments described in details above, but further variants, modifications and developments are possible within the scope of protection determined by the claims.

The invention claimed is:
1. A laryngeal mask, comprising
a head part and an inlet tube connected to the head part, and a passage is formed between a laryngeal opening of the head part and an inlet opening of the inlet tube, the laryngeal opening is adapted for fitting onto a trachea, and the inlet opening of the inlet tube is opposite the head part, and
an annular cushion connected to an outer part of the head part around the laryngeal opening,
the laryngeal mask further comprising a covering element encompassing the annular cushion, folding the annular cushion back to the head part and covering the laryngeal opening, the covering element is connected to the outer part of the head part at a part being towards the inlet tube from where the annular cushion connects to the outer part of the head part, and a releasable connection is formed circumferentially in the covering element or at the connection of the head part and the covering element, and a puller element being connected to an inner side of the covering element being towards the laryngeal opening, being arranged in the passage and being pullable from the inlet tube through the inlet opening, and being adapted for removing at least one part of the covering element through the inlet opening of the inlet tube by releasing the releasable connection.

2. The laryngeal mask according to claim 1, characterised in that the annular cushion is connected to a lateral part of the head part, which the lateral part of the head part faces in a direction at least partly parallel with a plane of the laryngeal opening.

3. The laryngeal mask according to claim 2, characterised in that the annular cushion is connected to the head part along two circumferential connection lines being parallel with each other.

4. The laryngeal mask according to claim 1, characterised in that the covering element is connected circumferentially to the outer part of the head part in a region towards the inlet tube from the connection of the annular cushion.

5. The laryngeal mask according to claim 1, characterised in that in an inflated state, the annular cushion has a circular cross section having an annular cushion radius, and a circumferential recess formed to match the annular cushion radius is formed in the head part for supporting the annular cushion at the part of the annular cushion which is connected to the head part in the inflated state of the annular cushion.

6. The laryngeal mask according to claim 1, characterised in that the releasable connection is formed in the covering element with one of the following:
   a thinning,
   a split perforation,
   a hole line perforation,
   a combination of thinning and split perforation, or a combination of thinning
   and hole line perforation.

7. The laryngeal mask according to claim 1, characterised in that the head part has a shape narrowing towards a front end of the head part and a rear end of the head part, and the puller element is connected to the covering element by two connecting feet, each of them extending towards the front end and rear end, respectively.

8. The laryngeal mask according to claim 7, characterised in that the connecting feet each have a tip substantially reaching the releasable connection and narrowing towards an end part.

9. The laryngeal mask according to claim 7, characterised in that the puller element is connected to the covering element through an oval base part having radial protruding parts.

10. The laryngeal mask according to claim 1, further comprising a strengthening yarn made from one piece, arranged longitudinally in the puller element and circumferentially in the covering element between the connection of the puller element and the releasable connection.

* * * * *